United States Patent
Fanier et al.

(10) Patent No.: US 12,076,082 B2
(45) Date of Patent: Sep. 3, 2024

(54) DEVICES FOR TREATING CALCIFIED HEART VALVES

(71) Applicant: MED-INNOV SAS, Bordeaux (FR)

(72) Inventors: Sylvain Fanier, Bordeaux (FR); Alexandre Couture, Sherbrooke (CA); Martin Brouillette, Sherbrooke (CA); Didier Tchetche, Toulouse (FR); Raymond Regnier, Pyla sur Mer (FR)

(73) Assignee: Med-Innov SAS, Bordeaux (FR)

( * ) Notice: Subject to any disclaimer, the term of this patent is extended or adjusted under 35 U.S.C. 154(b) by 480 days.

(21) Appl. No.: 17/290,569

(22) PCT Filed: Nov. 4, 2019

(86) PCT No.: PCT/IB2019/059427
§ 371 (c)(1),
(2) Date: Apr. 30, 2021

(87) PCT Pub. No.: WO2020/089876
PCT Pub. Date: May 7, 2020

(65) Prior Publication Data
US 2021/0378744 A1    Dec. 9, 2021

Related U.S. Application Data

(60) Provisional application No. 62/754,695, filed on Nov. 2, 2018.

(51) Int. Cl.
*A61B 18/26* (2006.01)
*A61B 17/22* (2006.01)
*A61B 18/00* (2006.01)

(52) U.S. Cl.
CPC .... *A61B 18/26* (2013.01); *A61B 2017/22025* (2013.01); *A61B 2017/22062* (2013.01);
(Continued)

(58) Field of Classification Search
CPC ..................................................... A61B 18/26
See application file for complete search history.

(56) References Cited

U.S. PATENT DOCUMENTS

2014/0046353 A1* 2/2014 Adams ............. A61B 17/22022
606/159
2017/0333122 A1* 11/2017 Rajagopalan .......... A61B 18/04

FOREIGN PATENT DOCUMENTS

| WO | 2010014515 A2 | 2/2010 |
| WO | 2016044651 A1 | 3/2016 |

OTHER PUBLICATIONS

International Search Report; International Searching Authority; International Patent Application No. PCT/IB2019/059427; dated Jan. 27, 2020; 5 pages.
(Continued)

*Primary Examiner* — Mallika D Fairchild
*Assistant Examiner* — Thien Jason Tran
(74) *Attorney, Agent, or Firm* — Taft Stettinius & Hollister LLP

(57) ABSTRACT

A balloon device for treating a calcified structure of a body tissue, including an elongated body extending between a proximal end and a distal end and having at least one lumen extending along at least a portion thereof and defining a fluid path, and at least one inflatable balloon secured to the elongated body and fluidly connected to the at least one lumen, with the at least one lumen being fluidly connectable to a fluid source for selectively inflating and deflating the at least one inflatable balloon, and with the at least one inflatable balloon, when being inflated, is positioned in close proximity to the calcified structure and vibrating, mechanical vibrations of the at least one inflatable balloon causes destructuration of the calcified structure.

14 Claims, 25 Drawing Sheets

(52) U.S. Cl.
CPC ............... *A61B 2018/0022* (2013.01); *A61B 2018/00369* (2013.01); *A61B 2018/00791* (2013.01); *A61B 2018/266* (2013.01)

(56) References Cited

OTHER PUBLICATIONS

Written Opinion of the International Searching Authority; International Searching Authority; International Patent Application No. PCT/IB2019/059427; dated Jan. 27, 2020; 7 pages.

* cited by examiner

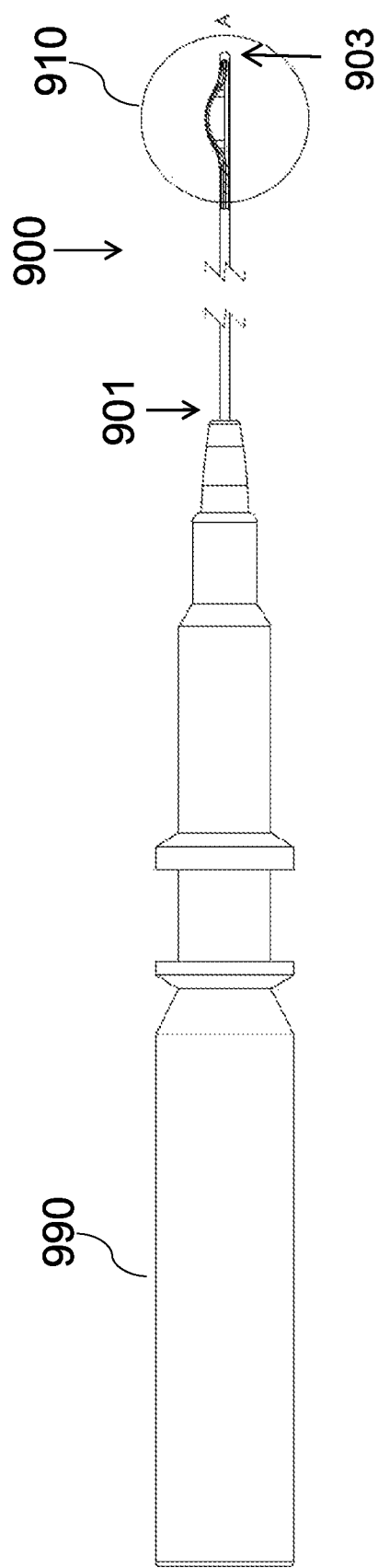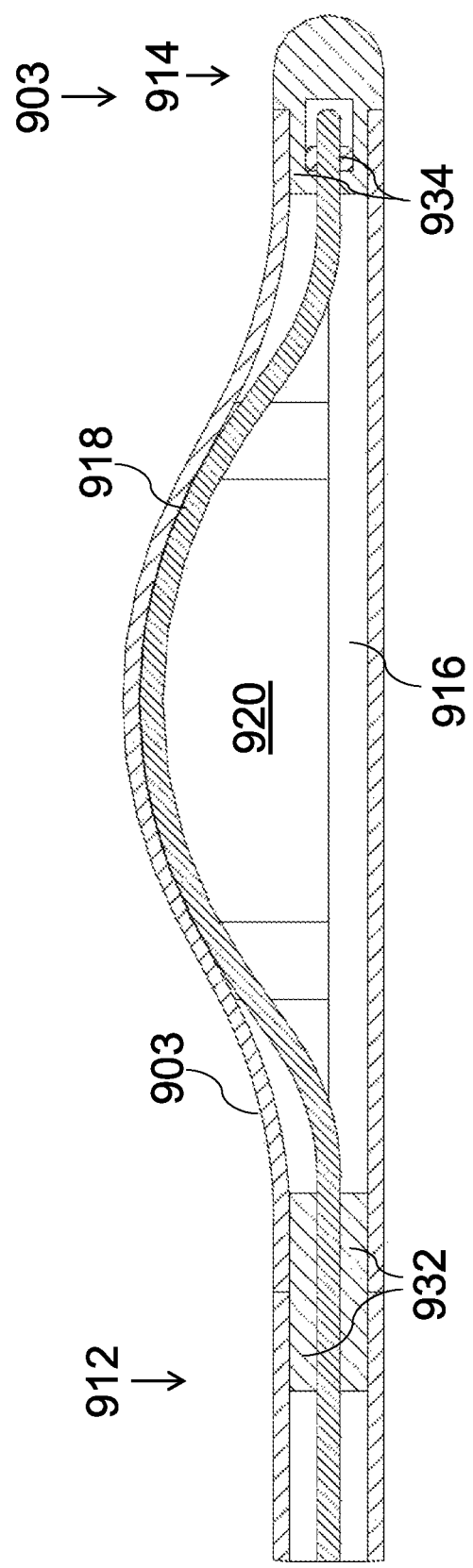
FIG. 9A
FIG. 9B

DEVICES FOR TREATING CALCIFIED HEART VALVES

CROSS REFERENCE TO RELATED APPLICATIONS

This application is a U.S. National Phase of International PCT Application No. PCT/IB2019/059427 filed Nov. 4, 2019, which claims the benefit of U.S. Provisional Patent Application Ser. No. 62/754,695 filed Nov. 2, 2018, the contents of each application are incorporated herein by reference in their entirety.

TECHNICAL FIELD

The present technology generally relates to methods and devices aiming at treating calcified heart valves or arteria walls to help them restore their functionality, and more particularly relates to a vibrating-balloon device and associated methods for treating such calcified structures.

BACKGROUND

A human heart is composed of four cavities: two atria and two ventricles. These cavities are separated by four valves, namely the tricuspid, pulmonary, mitral and aortic valves, opening and closing is a synchronized way, directing the blood flow from the atria to the ventricles then the pulmonary artery and the aorta. The aortic valve allows the oxygen-rich blood to exit the left ventricle and transit through the aorta and the arterial peripheral vasculature. Over time, the aortic valve may become narrowed and stenotic due to progressive calcium deposits within its leaflets. This pathology is called aortic stenosis: the aortic valve thickens, losing its elasticity and presenting with a narrowed opening area. Aortic stenosis (AS) is the most frequent valvular disease in western countries. Its prevalence increases with age, reaching up to 5% of subjects over the age of 75 years. Aortic stenosis generates an obstacle to the left ventricle output, leading to symptoms including shortness of breath, chest pains, syncope or sudden death. Two years after the appearance of the first symptoms, mortality reaches up to 50% in the absence of treatment. The impact of AS on quality of life, mortality and healthcare costs is important.

Surgical aortic valve replacement (SAVR) is the treatment of reference of aortic stenosis. The first SAVR using mechanical valves were performed by Harken (J. Thorac. Cardiovasc. Surg.; 1960 December; 40:744-62; Partial and complete prostheses in aortic insufficiency) and Starr (Starr A, Herr R H, Wood J A.; The present status of valve replacement; Special issue on the VII Congress of the International Cardiovascular Society held Sep. 14-18, 1965, in Philadelphia.; J. Cardiovasc. Surg.; 1965:95-103) in 1960.

Later, Carpentier (Mem. Acad. Chir. (Paris); 1967 Jun. 14; 93(19):617-22.; Use of aortic heterografts in treatment of mitral valvulopathy. Experimental basis and 1st clinical case; Carpentier A.) implanted the first biological aortic valves. Biological prosthesis, made of bovine or porcine pericardial tissue, are regularly implanted for AS.

Transcatheter aortic valve implantation (TAVI) is a valid alternative to SAVR in subjects at high-to intermediate mortality risk for conventional open-chest surgery. Two recent studies confirmed these results in a cohort of subjects at low risk. TAVI is the implantation, via a catheter inserted in the femoral artery, of a prosthesis composed by a metallic stent frame housing biological leaflets. The TAVI bioprosthesis is either crimped onto a balloon or retained within a capsule before expansion within the diseased aortic valve. The first-in-human TAVI was performed by Alain Cribier in 2002 ((Ann. Cardiol. Angeiol. (Paris); 2003 June; 52(3): 173-5; First human transcatheter implantation of an aortic valve prosthesis in a case of severe calcific aortic stenosis; Cribier A.)

In most valvular diseases, calcium structures develop within the valve leaflets, such as calcified nodules and bridge scaffolds, that thicken these leaflets. As a consequence, the leaflets have a reduced conformability, decreasing the efficiency of the aortic valve. Balloon aortic valvuloplasty (BAV) is a medical procedure aiming at restoring some degree of leaflets flexibility and improving the opening area of the diseased valve. In this medical procedure, a catheter is inserted through the femoral artery and advanced towards the aortic valve. Once the catheter placed within the stenotic aortic valve, a balloon located around the catheter is inflated, in order to push and open the leaflets of the calcified heart valve. Several inflations may be performed to enable adequate blood flow passage through the aortic valve. The balloon is then deflated and the catheter removed from the subject's body. BAV as a stand-alone procedure is rarely carried-out as its results are not sustained overtime. It may be part of the TAVI procedure as it often represents the first step before the deployment of the prosthesis, particularly in severely calcified valves. It is also used as a bridge to TAVI or SAVR in subjects with poor clinical condition or before emergent non-cardiac surgery. Despite positive clinical outcomes in the vast majority of the subjects, there are remaining limitations to TAVI, including non-exhaustively periprosthetic regurgitation, stoke, coronary obstruction and the need for a permanent pacemaker Most of these complications are related to the calcium burden. Bicuspid aortic valves represent a subgroup of subjects with poorer stent expansion after TAVI, due to heavily calcified nodules. There may be a need for devices targeting the calcium deposits within the aortic valve, as a single procedure or an adjunctive therapy to TAVI.

Surgeons have reported trials where calcifications within the cardiac valve leaflet have been removed mechanically or by ultrasound energy (1. Tex. Heart Inst. J. 1996; 23:85-7— Ultrasonic Decalcification of Calcified Valve and Annulus during Heart Valve Replacement, Mehmet Unal, MD/2. Tex. Heart Inst. J. 1996; 23:85-7; Journal of Therapeutic Ultrasound (2016) 4:10 DOI 10.1186/s40349-016-0053-z Shockwaves—influence of the experimental setup on the sound field and biological reaction, K Dietz-Laursonn). The cardiac valve function can be improved with these methods, but the procedure is very long and risks of calcium migration and stroke are high despite the use of filter devices positioned in the descending aorta.

These types of devices may also be used with other heart valves such as the mitral valve, the tricuspid valve and the pulmonary valve or with other valves of the human body which may have become stiff and/or thick from the accumulation of calcium deposits.

It would therefore be desirable to provide improved methods and devices that can safely and efficiently restore valve flexibility by softening the diseased valve tissue or fracturing the embedded calcified structures within the valve leaflets.

Moreover, similar problems may occur in arteries, where the progression of vascular disease can lead to the accumulation of calcified plaque on the inner lumen or within the walls. The presence of calcified structures may impair vascular function and prevent proper angioplasty to be performed.

There is therefore a need for improved methods and devices providing enhanced treatment of vascular calcified structures in arteries.

SUMMARY

According to a first broad aspect, there is provided a balloon device for treating a calcified structure of a body tissue comprising: an elongated body extending between a proximal end and a distal end and having at least one lumen extending along at least a portion thereof and defining a fluid path; and at least one inflatable balloon secured to the elongated body and fluidly connected to the at least one lumen, the at least one lumen being fluidly further connectable to a fluid source for selectively inflating and deflating the at least one inflatable balloon, the at least one inflatable balloon for treating the calcified structure when being inflated, being positioned in close proximity to the calcified structure and vibrating, mechanical vibrations of the at least one inflatable balloon causing destructuration of the calcified structure.

In one embodiment, the at least one inflatable balloon is positioned adjacent to the distal end of the elongated body.

In one embodiment, the at least one lumen is adapted to propagate therein an oscillatory pressure fluid, the fluid source being adapted to generate pressure variations within the oscillatory pressure fluid, the pressure variations causing the mechanical vibrations of the at least one inflatable balloon.

In another embodiment, the elongated body is connectable to a vibration source for inducing mechanical vibrations into the at least one inflatable balloon when inflated.

In one embodiment, the at least one balloon is adapted to receive an electrically conductive fluid therein from the fluid source, the balloon device further comprising at least two vibration electrodes electrically connectable to the vibration source, the vibration source being an electrical power source, wherein the at two electrodes are operable to receive electrical power from the electrical power source to generate plasma shock waves within the electrically conductive fluid inside the at least one inflatable balloon to induce the mechanical vibrations.

In one embodiment, the balloon device further comprises at least one piezoelectric transducer electrically connectable to the vibration source, the vibration source being an electrical power source, wherein the at least one piezoelectric transducer is operable to receive electrical power from the electrical power source to generate the mechanical vibrations of the at least one inflatable balloon.

In one embodiment, the balloon device further comprises at least one transducer and at least one optical waveguide operatively connected to the vibration source, the vibration source being a light source, wherein the at least one transducer is operable to receive light from the light source so as generate the mechanical vibrations of the at least one inflatable balloon.

In one embodiment, the at least one optical waveguide comprises at least one optical fiber and the light source comprises a pulsed laser source.

In one embodiment, the at least one inflatable balloon is rotatably secured to the elongated body, the at least one inflatable balloon being rotatable about a longitudinal axis of the elongated body.

In one embodiment, the balloon device further comprises at least one temperature sensor for measuring a temperature within the at least one balloon.

In one embodiment, the balloon device further comprises at least one monitoring sensor for measuring at least one of a filling status of the at least one inflatable balloon and a pressure within the at least one inflatable balloon.

In one embodiment, the at least one monitoring sensor comprises one of a pressure sensor and an impedance sensor.

In one embodiment, the elongated body further comprises a proximal opening, a distal opening and a blood flow lumen defining a fluid path between the proximal opening and the distal opening for enabling blood flow between the proximal end and the distal end of the elongated body.

In one embodiment, the elongated body further comprises a wire lumen extending within the elongated body and being sized and shaped for receiving a wire therein.

In one embodiment, an outer surface of the at least one inflatable balloon is provided with at least one geometrical deformation.

In one embodiment, the at least one inflatable balloon comprises at least a portion having at least one of: a different rigidity than a remainder of the at least one inflatable balloon, and a different thickness than the remainder of the at least one inflatable balloon.

According to another broad aspect, there is provided a system for treating a calcified structure of a body tissue comprising: a vibrating-balloon device comprising: an elongated body extending between a proximal end and a distal end and having at least one lumen extending along at least a portion of the elongated body and defining a fluid path therebetween; at least one inflatable balloon connected to the at least one lumen adjacent to the distal end of the elongated body, the at least one inflatable balloon for treating the calcified structure when being inflated, being positioned in close proximity to the calcified structure and vibrating, mechanical vibrations of the at least one inflatable balloon causing destructuration of the calcified structure; and a fluid source fluidly connectable to the at least one lumen and operable to selectively inflate and deflate the at least one inflatable balloon.

In one embodiment, the at least one inflatable balloon is positioned adjacent to the distal end of the elongated body.

In one embodiment, the fluid source is adapted to generate pressure variations within the oscillatory pressure fluid, the pressure variations causing the mechanical vibrations of the at least one inflatable balloon.

In one embodiment, the system further comprises a vibration source for inducing mechanical vibrations into the at least one inflatable balloon when inflated.

In one embodiment, the vibration source comprises an electrical power source and the fluid source is adapted to provide an electrically conductive fluid therein from the fluid source, the balloon device further comprising at least two vibration electrodes electrically connectable to the vibration source, wherein the at two electrodes are operable to receive electrical power from the electrical power source to generate plasma shock waves within the electrically conductive fluid inside the at least one inflatable balloon to induce the mechanical vibrations.

In one embodiment, the vibration source comprises an electrical power source, the balloon device further comprising at least one piezoelectric transducer electrically connectable to the vibration source, wherein the at least one piezoelectric transducer is operable to receive electrical power from the electrical power source to generate the mechanical vibrations of the at least one inflatable balloon.

In one embodiment, the vibration source comprises a light source and the balloon device further comprises at least one transducer and at least one optical waveguide operatively connected to the light source, wherein the at least one transducer is operable to receive light from the light source so as generate the mechanical vibrations of the at least one inflatable balloon.

In one embodiment, the at least one optical waveguide comprises at least one optical fiber and the light source comprises a pulsed laser source.

In one embodiment, the at least one inflatable balloon is rotatably secured to the elongated body, the at least one inflatable balloon being rotatable about a longitudinal axis of the elongated body.

In one embodiment, the balloon device further comprises at least one temperature sensor for measuring a temperature within the at least one balloon.

In one embodiment, the balloon device further comprises at least one monitoring sensor for measuring at least one of a filling status of the at least one inflatable balloon and a pressure within the at least one inflatable balloon.

In one embodiment, the at least one monitoring sensor comprises one of a pressure sensor and an impedance sensor.

In one embodiment, the elongated body further comprises a proximal opening, a distal opening and a blood flow lumen defining a fluid path between the proximal opening and the distal opening for enabling blood flow between the proximal end and the distal end of the elongated body.

In one embodiment, the elongated body further comprises a wire lumen extending within the elongated body and being sized and shaped for receiving a wire therein.

In one embodiment, an outer surface of the at least one inflatable balloon is provided with at least one geometrical deformation.

In one embodiment, the at least one inflatable balloon comprises at least a portion having at least one of: a different rigidity than a remainder of the at least one inflatable balloon, and a different thickness than the remainder of the at least one inflatable balloon.

According to a further embodiment, there is provided method for treating a calcified structure of a body tissue, the method comprising: providing a vibrating-balloon device comprising: an elongated tubular body extending between a proximal end and a distal end and having at least one lumen extending along at least a portion of the elongated tubular body and defining a fluid path therebetween, and at least one inflatable balloon secured to the elongated tubular body and fluidly connected to the at least one lumen; placing the inflatable balloon in close proximity to the body tissues; and inflating the at least one inflatable balloon using a fluid source and generating mechanical vibrations within the at least one inflated balloon thereby inducing mechanical vibrations of the calcified structure upon contact of the balloon with the body tissues to destructure the calcified structure.

In one embodiment, the elongated tubular body further comprises an inner lumen for receiving a guidewire; and wherein said placing the inflatable balloon in close proximity to the body tissues is performed using the guidewire.

In one embodiment, the generating the mechanical vibrations within the at least one inflatable balloon is performed by generating pressure variations into a fluid using the fluid source.

In one embodiment, the generating the mechanical vibrations within the at least one inflatable balloon is performed using a vibration source.

In one embodiment, the method further comprises, before the oscillatory inflating the balloon: identifying resonance-inducing parameters for a static and a dynamic pressure variation that promote structural resonance of the calcified structure.

In one embodiment, the method further comprises: moving the inflatable balloon to a different region of the tissues; and repeating the oscillatory and the moving until each calcified structure has been treated.

BRIEF DESCRIPTION OF THE DRAWINGS

In order that the technology may be readily understood, embodiments of the technology are illustrated by way of example in the accompanying drawings.

FIG. 9A is a schematic elevation view taken from the right of a steerable vibrating-balloon device in accordance with non-limiting embodiments of the present technology.

FIG. 9B is an enlarged view of a tip of the vibrating-balloon device of FIG. 9A.

Further details of the technology and its advantages will be apparent from the detailed description included below.

DETAILED DESCRIPTION

In the following description of the embodiments, references to the accompanying drawings are by way of illustration of examples by which the technology may be practiced. It will be understood that other embodiments may be made without departing from the scope of the technology disclosed.

In the following, there is described a vibrating-balloon device, a vibrating-balloon system and a method for treating calcified structures using the vibrating-balloon device/system.

In one embodiment, the vibrating-balloon device of the present technology is particularly well suited to effectively and rapidly treat calcified valves and arteries without dislodging tissue particles nor damaging surrounding healthy tissue, as it will become apparent below.

Normal Aortic Valve

Figure 1A:
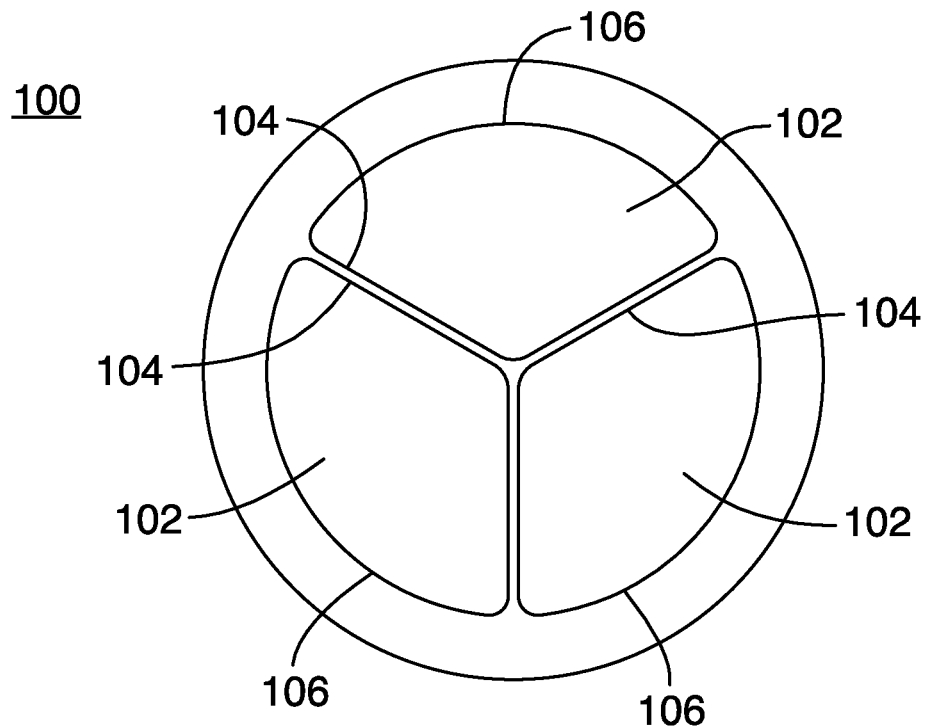
FIG. 1A is a schematic top view of a normal aortic valve.

Referring to FIG. 1A, there is shown a top view of a normal aortic valve 100 in a closed configuration. The illustrated valve 100 has 3 flexible leaflets 102 with each leaflet 102 having a free margin 104 and an attached margin 106 at the wall of the aorta. In normal use, each valve leaflet 102 deforms around its attached margin 106 such that its free margin 104 moves in and out of the flow. When the margins 104 of all the leaflets 102 meet, then the valve closes, and when the margins 104 move away from each other, then the valve opens. The skilled addressee will appreciate that other valves may be provided with only 2 flexible leaflets 102. The vibrating-balloon device of the present technology is also well suited to effectively treat such valves, at it will become apparent upon reading the present description.

Calcified Aortic Valve

Figure 1B:
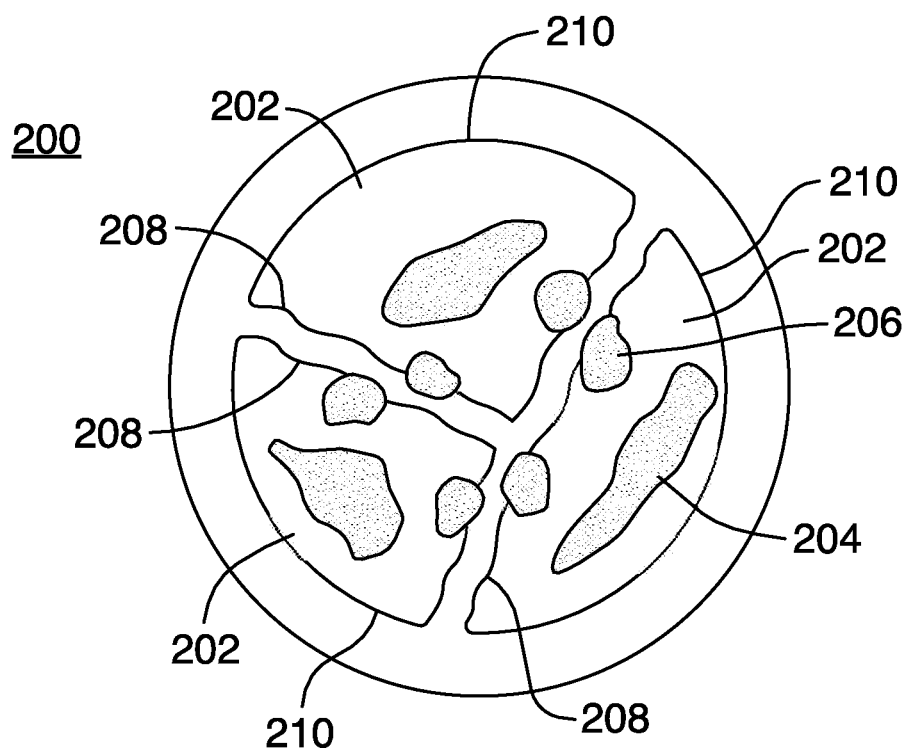
FIG. 1B is a schematic top view of a calcified aortic valve.

Referring to FIG. 1B, there is shown a top view of a calcified aortic valve 200 in the closed configuration. The illustrated valve 200 has 3 leaflets 202 with free margins 208 and attached margins 210. Each valve leaflet 202 articulates with the free margins 208 of the other leaflets 202 when the valve closes, where all the margins 208 normally meet to close the aorta. Calcified structures, such as plaques or nodular deposits, may accumulate on the surface of or within the leaflets 202 which may stiffen the valve 200, and thereby reduce its flexibility and impair its ability to open and close effectively. Calcified nodular deposits 206 may accumulate along the free margins 208 of the leaflets 202, which may prevent from closing properly when the margins 208 meet. Calcified plaques or nodules 204 present within the leaflets 202 may stiffen the leaflets which may reduce the flow passage of the valve 200 in the open position and prevent the valve 200 from closing properly.

Figure 1C:
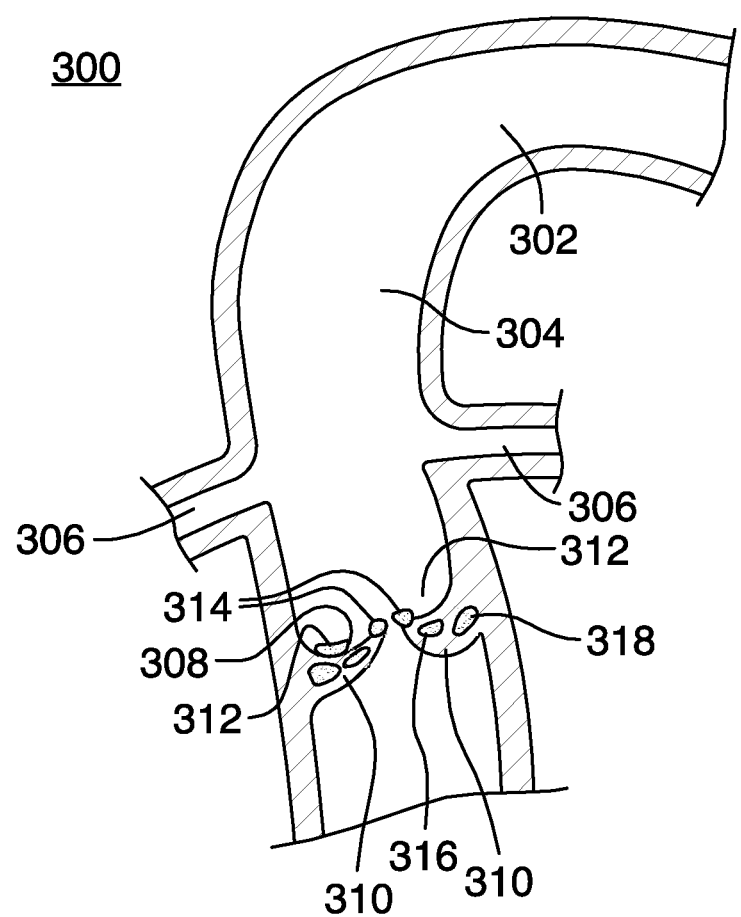
FIG. 1C is a schematic lateral cross-sectional view of the anatomy of a calcified aortic valve, ascending aorta and aortic arch.

Referring now to FIG. 1C, there is shown a side cross-sectional view of a calcified aortic valve 300 in the closed configuration, including the ascending aorta 304, aortic arch 302 and coronary ostia 306. Each valve leaflet 310 of the valve 300 has a concave part 312. Calcified nodular deposits 314 may accumulate along the free margins of the leaflets 310, and calcified plaques 318 or nodules 316 may also form within the leaflets 310, as well as plaques 308 on the leaflets surfaces. As previously mentioned, the calcified structures developing on or within the valve leaflets may prevent the valve from operating correctly.

Vibrating-Balloon Device

Figure 2A:
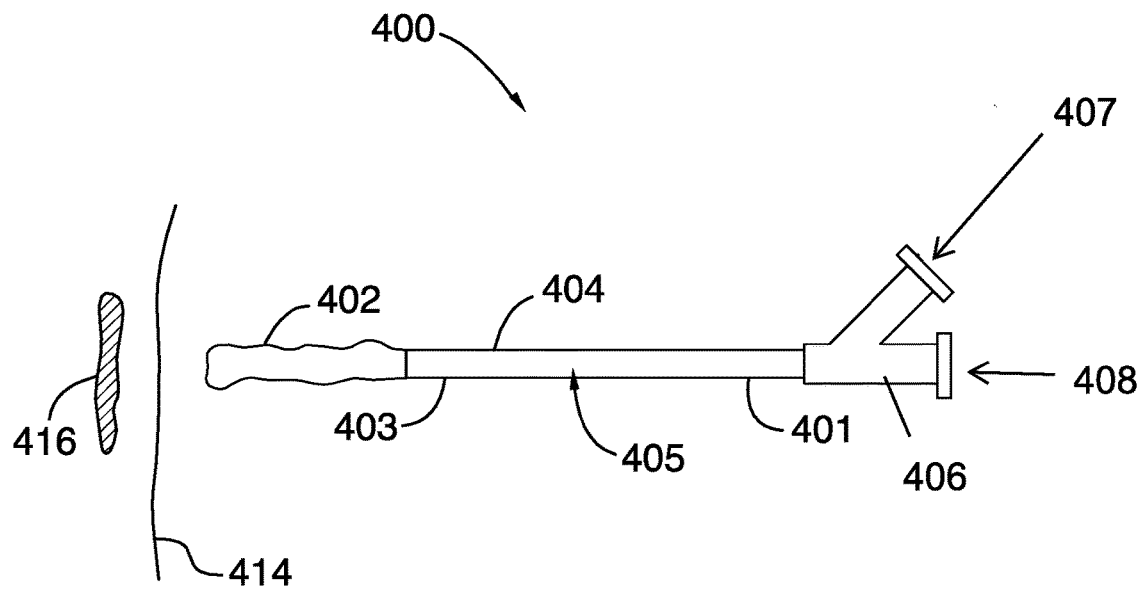
FIG. 2A is a schematic side view of a vibrating-balloon device, in a deflated state, and of a calcified tissue region in accordance with non-limiting embodiments of the present technology.

Reference is now made to FIG. 2A which shows a vibrating-balloon device 400 for treating calcified structures 416 of body tissues, and of a calcified tissue region 414, such as an aortic valve, according to one exemplary embodiment. As it will become apparent, the vibrating-balloon device 400 is intended to destructure, i.e., weaken, fracture and/or crack, these calcified deposits 416 without removing them, which will help restore some of the valve original flexibility and thereby improve its function, while avoiding harmful emboli to be produced. The vibrating-balloon device 400 is adapted to vibrate an inflatable balloon 402, once inflated, in contact with the valve leaflets to induce mechanical vibration of the calcified structures within until their failure.

As shown in FIG. 2A, the vibrating-balloon device 400 has an elongated body 404 extending between a proximal end 401 and a distal end 403 and a lumen 405 defining a fluid path therebetween. The lumen 405 extends between an inlet and an outlet. The inlet located at the proximal end 401 is fluidly connectable to a source of fluid while the outlet is fluidly connected to the interior of the balloon 402 so as to inject fluid in and out of the balloon 402. The elongated body 404 has a tubular shape but other shapes may be possible as would be recognized by a person skilled in the art.

In the illustrated embodiment, the vibrating-balloon device 400 also has an inflatable balloon 402 mounted adjacent to the distal end 403 of the elongated body 404. In the illustrated embodiment, the inflatable balloon 402 is in a deflated state and is sealed to the distal end 403 of the elongated body 404. The side port 407 of the Y-shape connector 406 connected to the proximal end 401 of the vibrating-balloon device 400 is connectable to a source of fluid (not shown). As described in greater detail below, the source of fluid may comprise a single fluid source unit which may then be referred as an oscillatory pressure source to be used for both inflating/deflating and vibrating the balloon 402. Alternatively, the source of fluid may comprise two distinct fluid source units, i.e., a first source of fluid providing a static pressure fluid for selectively inflating and deflating the balloon 402 and a second source of fluid (or source of vibrations) providing an oscillatory pressure fluid for oscillatory varying the pressure of the fluid within the balloon 402 once inflated.

The oscillatory variation of the pressure of the fluid created by the source of fluid generates mechanical waves that propagate from the source of fluid within the lumen 405 up to the interior of the balloon 402. The mechanical waves while reaching the wall of the balloon 402 generate a displacement of the wall of the balloon 402, thereby vibrating the balloon 402.

In the illustrated embodiment, a Y-shaped connector 406 is connected to the proximal end 401 of the elongated body 404 so as to fluidly connect the vibrating-balloon device 400 to two sources of fluid (i.e., to a first source of fluid for selectively inflating and deflating the balloon 402 and a second source of fluid for vibrating the balloon 402). The connector 406 comprises a first inlet 407 fluidly connectable to a given one of the two sources of fluid and a second inlet fluidly connectable to the other source of fluid. For example, a source of static pressure fluid may be connected to the first inlet 406 while a source of oscillatory pressure fluid may be connected to the second inlet 408.

The source of oscillatory pressure fluid is operable to oscillatory inflate the inflatable balloon 402 through the fluid path 405 of the elongated body 404, as detailed below. Once the balloon 402 is inflated using the source of static pressure fluid, the source of oscillatory pressure fluid generates pressure variations into the fluid indoor to vibrate the wall of the inflatable balloon 402, thereby inducing mechanical vibrations of the calcified structures 416 of a calcified tissue region 414 upon contact of the balloon 402 with the body tissues or upon positioning the balloon 402 in close proximity with the calcified structures 416 in order to destructure the calcified structures 416.

Figure 2B:
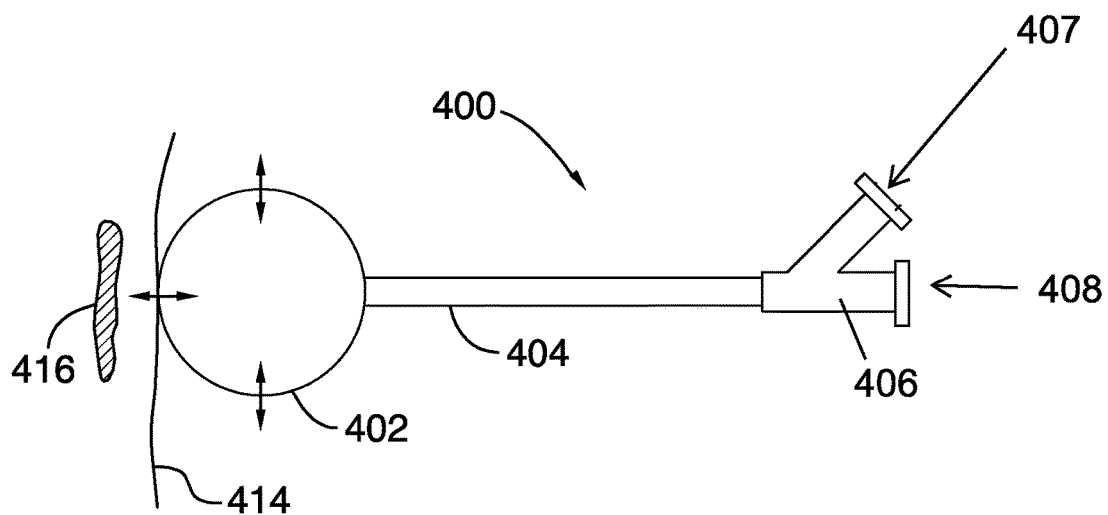
FIG. 2B shows the vibrating-balloon device of FIG. 2A, in an inflated state.

Referring now to FIG. 2B, the inflatable balloon 402 is shown in an inflated state. The inflatable balloon 402 may be filled with a sterile liquid, such as a saline solution or a radiopaque contrast agent, or a sterile medical gas, as known in the art. When the source of vibration is activated, this causes the balloon 402 to expand, contract resulting a vibration. Because at least some calcified structures 416 are inherently fragile materials, when the wall of the balloon 402 is placed in contact with a calcified tissue region 414, the mechanical vibrations from the balloon 402 are transferred to the calcified tissues and calcified structures 416 within and, especially when the vibrations are at the resonance frequency or frequencies of the calcified structures 416, as better detailed below, these vibrations may crack, break or generally destructure these calcified structures 416, making the tissue more flexible after treatment.

Figure 2C:
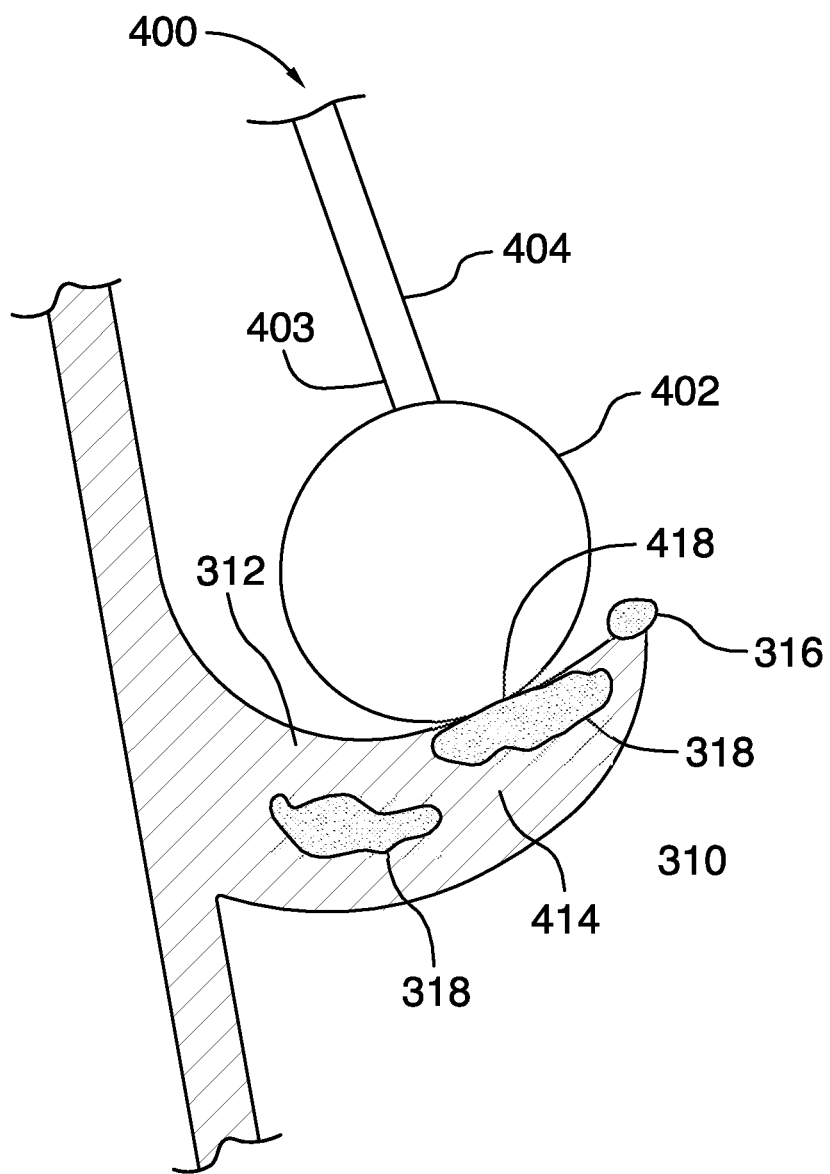
FIG. 2C is another schematic side view of the vibrating-balloon device of FIG. 2A, in an inflated state.

Referring to FIG. 2C, there is shown the balloon 402 of the vibrating-balloon device 400 in operation treating a calcified valve leaflet 310. The balloon 402 and the distal end 403 of the elongated body 404 are inserted into an artery and advanced through the aorta until the balloon 402 is brought near and inflated in the concave part 312 of the valve leaflet 310 having a calcified tissue region 414, resulting in a contacting region 418 between the outer surface of the balloon 402 and the valve leaflet 310. The proximal end 401 of the elongated body 404 and the source of fluid remain outside the body of the subject. The pressure variations from the source of fluid are transmitted to the balloon 402 via the elongated body 404 which produces mechanical vibrations of the wall of the balloon 402. The mechanical vibrations from the balloon 402 are transferred to the calcified tissue region 414 and calcified plaques 318 and nodules 316 and these vibrations may crack, break or generally destructure these plaques and nodules, making the valve leaflet tissue more flexible and thereby improving valve function.

Efficient transmission of mechanical vibrations from the balloon 402 to the calcified tissue region 414 requires adequate mechanical coupling between the two, ensured by close contact between the outer surface of the inflated balloon 402 and the surface of the tissue region 414 at the contacting region 418. To achieve this, the size, shape, materials and construction of the balloon 402 may be selected such that when the balloon 402 is positioned at the proper position and then inflated with a liquid or gas, at least a portion of the outer surface of the balloon 402 is in close direct contact with the surface of the tissue region 414 to be treated.

Like many other vascular treatment devices, in one embodiment, the elongated body 404 of the vibrating-balloon device 400 may be constructed from shape-memory materials, such as shape-memory alloys and/or shape-memory polymers, such that it may be advanced through the vasculature in a compact configuration and, when at the proper location, deployed in an expanded configuration that may position the outer surface of the inflated balloon 402 in adequate contact with the tissue region to be treated 414. The elongated body 404 may be flexible enough to deform when advanced with the vasculature but not too compliant as to absorb the vibrations generated by the source of fluid. For example, in one embodiment, the elongated body 404 may comprise a mesh material which offers low longitudinal rigidity and high torsional rigidity for deliverability and high circumferential rigidity to maximize pressure transmission.

Balloon Outer Surface

Figure 3:
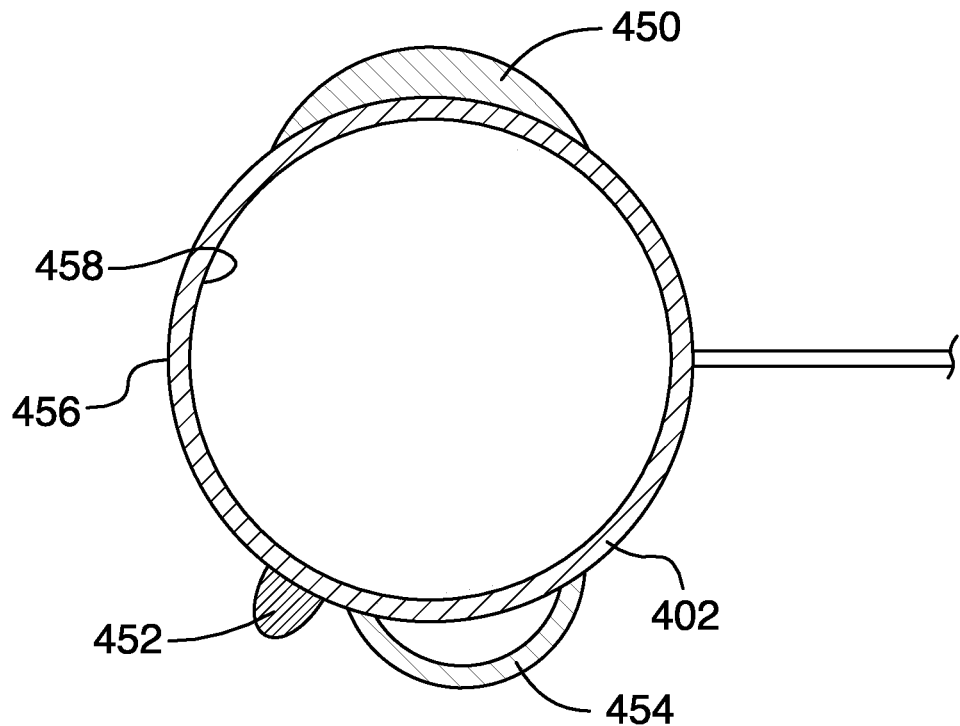
FIG. 3 is a schematic cross-sectional side view of a vibrating-balloon device, the balloon being provided with surface features in accordance with non-limiting embodiments of the present technology.

Referring now to FIG. 3, in a further embodiment, the outer surface 456 of the wall of the balloon 402 may be equipped with geometrical features, deformations or protrusions adapted to prevent the inflated balloon 402 from blocking blood flow into the coronary ostia 306 and/or into the ascending aorta 304 illustrated in FIG. 1C. These features or deformations may take the shape of ridges 450, bumps 452 or struts 454, which may be integrally molded as part of the balloon material, or they may be made from a different material than the balloon 402. For example, they can be made from shape-memory material arranged at the outer surface 456 of the balloon, which, when deployed at the site to be treated, becomes a ridge, bump or strut. In another example, the shape-memory material may be inside the balloon 402 which, when deployed on the inner surface 458 of the balloon, produces one or multiple ridges, bumps or struts on the outer surface 456 of the balloon 402.

In still a further embodiment, the construction of the balloon 402 may be such that preferential deformations under pressure inflation may be produced, for example in order to ensure optimal contact between a portion on the outer surface of the balloon and the surface of the region to be treated.

Balloon Shapes

Figure 4A:
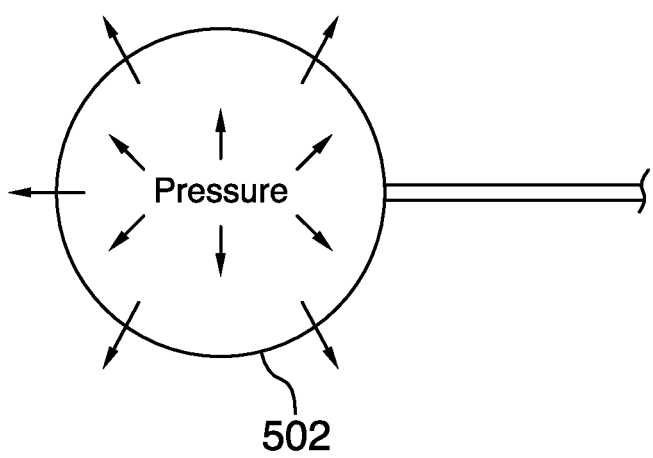
FIG. 4A is a schematic side view of another balloon of a vibrating-balloon device showing a uniform balloon inflation in accordance with non-limiting embodiments of the present technology.
Figure 4B:
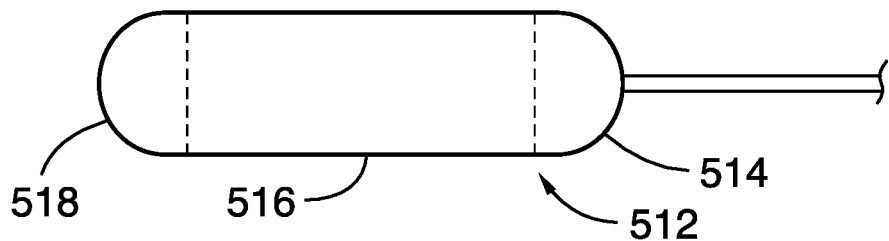
FIG. 4B is a schematic side view of another balloon of a vibrating-balloon device having an elongated shape in accordance with non-limiting embodiments of the present technology.
Figure 4C:
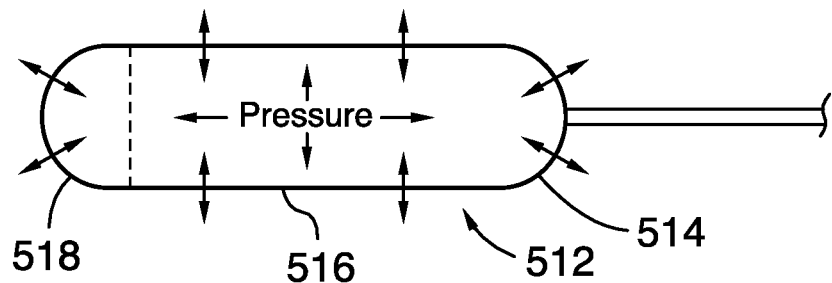
FIG. 4C is another schematic side view of the vibrating-balloon device of FIG. 4B.
Figure 4D:
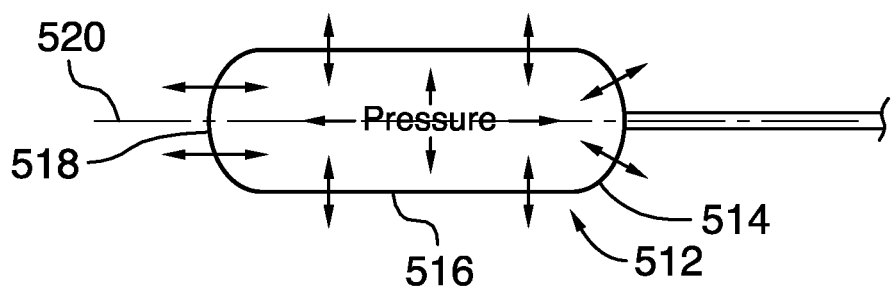
FIG. 4D is a further schematic side view of the vibrating-balloon device of FIG. 4B.

FIG. 4A to 4D show various other embodiments of an inflatable balloon. FIG. 4A shows a balloon 502 having such construction that, upon applied inflation pressure, the balloon 502 deforms uniformly in a three-dimensional space and has a spherical shape. FIG. 4B shows an elongated inflated balloon 512 having a proximal end 514, a central portion 516 and a distal end 518. FIG. 4C shows the balloon 512 of FIG. 4B with a more rigid (i.e., less flexible) proximal end 514 and central portion 516 than the distal end 518, such that upon applied pressure within the balloon 512, the deformation of the distal end 518 is much greater than that of the proximal end 514 and central portion 516. In another embodiment shown in FIG. 4D, the distal end 518 is almost flat and perpendicular to the longitudinal axis 520 of the balloon 512 and much more flexible than the central portion 516 and proximal end 514, such that upon applied pressure within the balloon 512, the deformation of the distal end 518 is much greater than that of the proximal end 514 and central portion 516, and in the general direction of the longitudinal axis 520 of the balloon 512.

Other combination of rigidities may be possible. For example, in one embodiment the proximal end 514 is more rigid than the central portion 516 and distal end 518 such that upon applied pressure within the balloon, the deformation of the distal end 518 and central portion 516 is much greater than that of the proximal end 514. In another embodiment, the proximal end 514 and distal end 518 are more rigid than the central portion 516 such that upon applied pressure within the balloon, the deformation of the central portion 516 is much greater than that of the distal end 518 and proximal end 514 and essentially in the radial direction perpendicular to the longitudinal axis 520 of the balloon.

Similarly, specific regions of the balloon surface may be made more rigid or less rigid than the rest of the balloon surface. For example, in one embodiment, at least one circular region (not shown) on the balloon surface may be more flexible than the rest of the balloon such that upon applied pressure within the balloon, the deformation of the at least one circular region is much greater than that of the rest of the balloon surface. These specific regions may have other shapes than circular, such as ellipsoidal, triangular, square and hexagonal as non-limitative examples. There may be a single specific region or a plurality of them, each having the same or different shapes.

In a further embodiment, the rigidities of the various portions of the balloon may be tailored by using a single balloon material of varying thickness, such that the more rigid portions may be made of thicker material. In another embodiment, the rigidities of the various portions of the balloon may be tailored by using a single balloon material having different geometrical features, such as ribs and meshes, such that the more rigid portions may have different geometrical features than the more flexible portions. In still another embodiment, the rigidities of the various portions of the balloon may be tailored by using different materials in the various portions of the balloon, such that the more rigid portions may use more rigid materials than the more flexible portions. It should be noted that the rigidities of the various portions of the balloon may also be tailored by a combination of materials, material thickness and geometrical features.

As it should be appreciated, combinations of specific rigidities for the different portions of the balloon along with surface features such as the ridges, bumps or struts of FIG. 3 may promote preferential motions of the surface features either in a direction parallel to the longitudinal axis 520 of the balloon 512, in a direction perpendicular to the longitudinal axis 520 of the balloon 512 or in a direction at another angle with respect to the longitudinal axis 520 of the balloon 512.

In one embodiment, the balloon and the elongated body of a vibrating-balloon device are provided with one or more markers (not shown) visible under x-ray or ultrasound imaging. For example, the markers may be radiopaque bands or wires attached to the balloon or to the elongated body, made from radiopaque material such as gold or platinum, for example, or they may be polymer material doped with radiopaque particles. In another embodiment, the material of the balloon and/or the elongated body may comprise a polymer doped with radiopaque particles for example.

In one embodiment, a vibrating-balloon device such as described above and which is provided with a single balloon mounted with an elongated body may be used to treat a single valve leaflet or all the leaflets at a time. To treat more than one valve leaflet within a valve may require treating a single valve leaflet at a time then moving the device from one leaflet to the next.

Figure 7A:
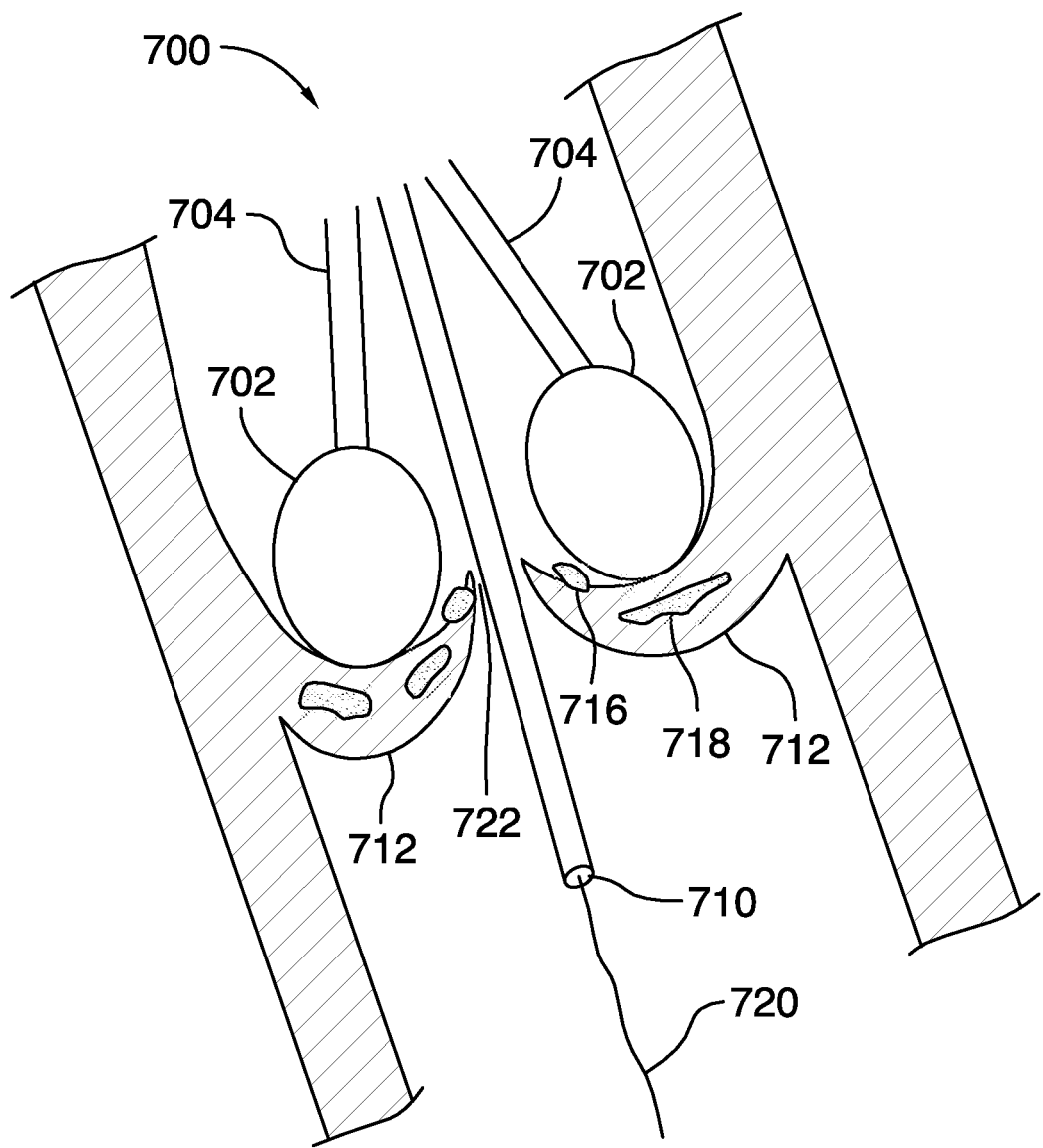
FIG. 7A is a schematic cross-sectional side view of a multiple vibrating-balloons device, provided with an inner lumen allowing a guide-wire introduction, and of calcified valve leaflets in accordance with non-limiting embodiments of the present technology.
Figure 7B:
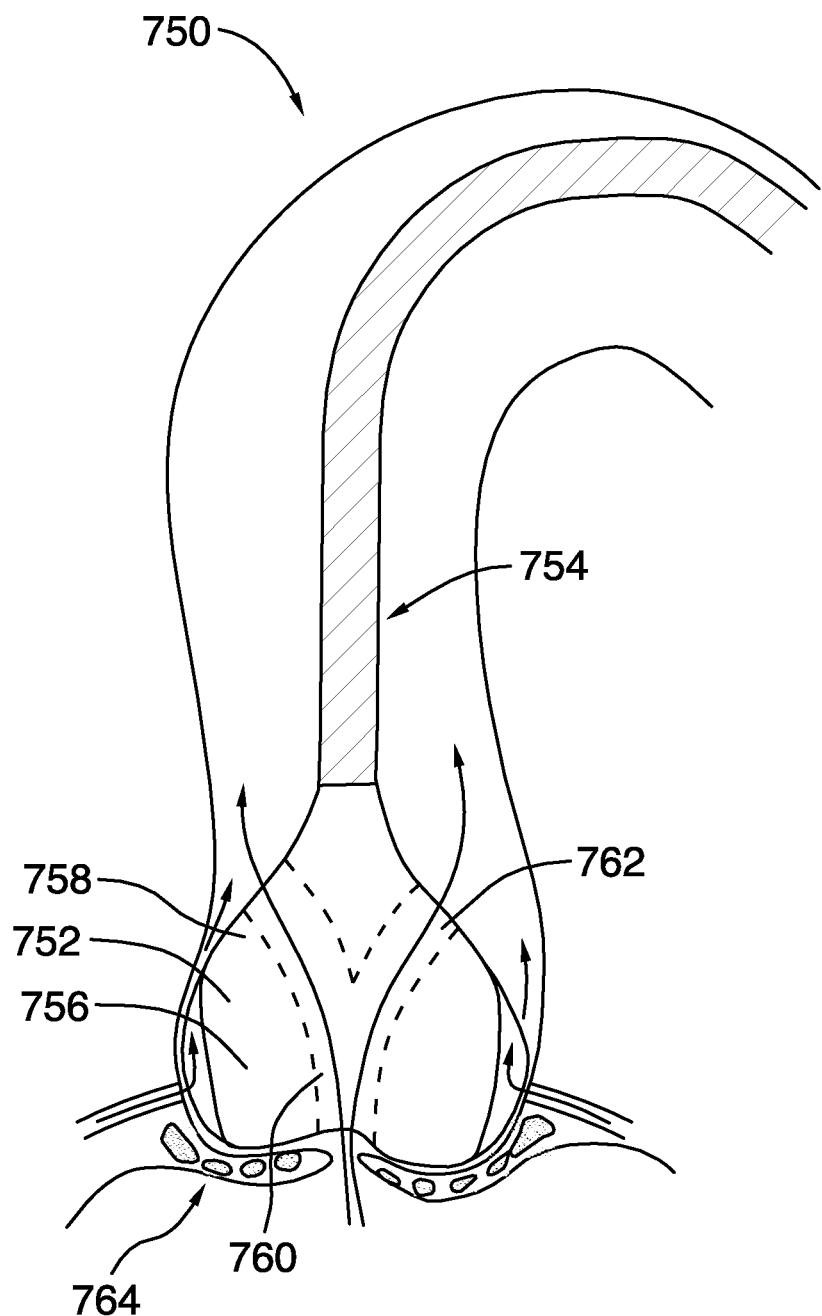
FIG. 7B is a schematic cross-sectional side view of a multi-lobe vibrating-balloon device and of a calcified valve in accordance with non-limiting embodiments of the present technology.

In another embodiment, a vibrating-balloon device is provided with multiple balloons or a multi-lobes balloon, which may allow for the treatment of a single valve leaflet and/or the simultaneous treatment of multiple leaflets, as illustrated in FIG. 7A and FIG. 7B described below. In one embodiment, each balloon may be attached to the same elongated body operatively connected to a single source of fluid, or, in another embodiment, each balloon may be attached to a distinct elongated body, each operatively connected to a distinct source of fluid. In yet another embodiment, each balloon may be attached to a distinct elongated body, with a single source of fluid operatively connected to each of the elongated tubular bodies.

To treat a single valve leaflet at a time with a multiple balloon device, the device may be advanced into the aorta until all the balloons are near the concave part of a calcified valve leaflet, with at least one balloon in contact with the calcified valve leaflet and the other balloons either in contact with the calcified valve leaflet, with the wall of the aorta and/or the other valve leaflets. This may allow better positioning of the at least one balloon in contact with the calcified valve leaflet to be treated, leading to more efficient treatment, and/or preventing blood flow blockage into the aorta and/or a coronary artery.

To treat multiple valve leaflets with a multiple balloon device, the device may be advanced into the aorta until all the balloons are near the valve, with at least one balloon in contact with each of at least two calcified valve leaflets and the other balloons either in contact with the same calcified valve leaflets, with the wall of the aorta and/or other valve leaflets. This may allow better positioning of each balloon in contact with a calcified valve leaflet, leading to more efficient treatment, and/or preventing blood flow blockage into the aorta and/or a coronary artery.

Vibrating-Balloon Device Insertable Over a Wire

Figure 5:
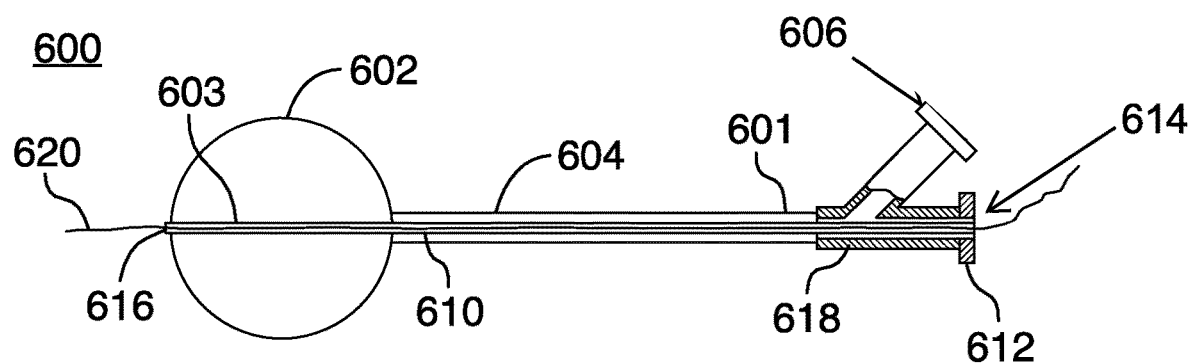
FIG. 5 is a schematic side view of another vibrating-balloon device provided with an inner lumen allowing for guidewire insertion, and a Y-shape connector allowing fluid injection in a second inner lumen to inflate and connect an hydraulic pump to vibrate the vibrating balloon device, according to another embodiment.

Referring now to FIG. 5, there is shown a vibrating-balloon device 600 having a balloon 602, an elongated body 604 fluidly connectable to a source of fluid, a first inner lumen 610 and a second inner lumen (not shown). The elongated body 604 extends between a proximal end 601 and a distal end 603. The first inner lumen 610 extends from the proximal end 601 to the distal end of the elongated body 604 while the second inner lumen extends from the proximal end 601 of the elongated body 604 up to the balloon 602. The first inner lumen 610 is shaped and sized so as to receive a wire 620 such as a guidewire therein. The second inner lumen is shaped and sized for receiving fluid therein and propagate fluid in and out of the balloon 602.

In the illustrated embodiment, a Y-shaped connector 618 is used for fluidly connecting the second inner lumen of the elongated body 604 to at least one source of fluid and allowing the insertion of the wire through the first inner lumen 610. The Y-shaped connector 618 comprises a first inlet 606 that is fluidly connectable to a source of fluid and fluidly connected to the second inner lumen when the connector 618 is connected to the elongated body 604. The Y-shaped connector 618 comprises a second inlet 612 provided with a wire port 614 that communicates with the first inner lumen 610 when the connector 618 is connected to the elongated body 604. As a result, the wire 620 may run through the elongated body 604 from the wire port 614 of the Y-shaped connector 618 to a distal wire port 616 located at the distal end 603 of the elongated body 604, thereby allowing for the vibrating-balloon device 600 to be inserted over a wire 620 such as a guidewire already in place across the valve, according to one embodiment.

Figure 6A:
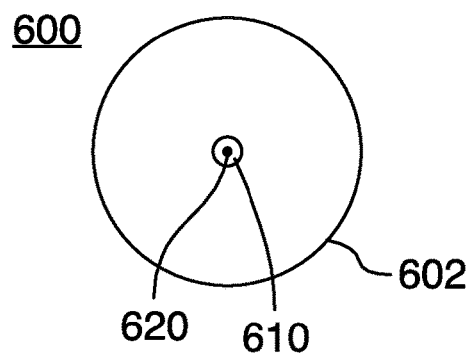
FIG. 6A is a schematic front view of a vibrating-balloon device provided with an inner concentric lumen, according to one embodiment.
Figure 6B:
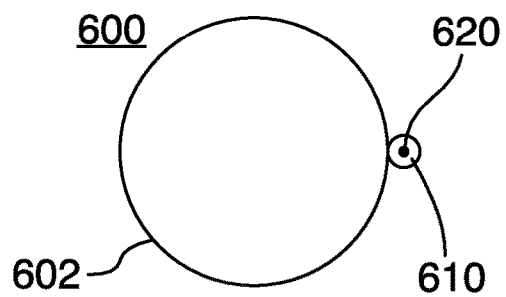
FIG. 6B is a schematic front view of a vibrating-balloon device provided with an inner lumen on the outside surface of the balloon in accordance with non-limiting embodiments of the present technology.

FIG. 6A shows the distal end view of a vibrating-balloon device 600 for which the first inner lumen 610 is concentrically located within the elongated body 604 and within the balloon 602, while FIG. 6B shows the distal end view of a vibrating-balloon device 600 for which the inner lumen 610 is located on the outside surface of the balloon 602. Various other embodiments may be considered. For example, the wire lumen 610 may be provided at an intermediate position between the balloon concentric position shown in FIG. 6A and the balloon surface position shown in FIG. 6B. In yet another embodiment, the inner lumen 610 may not be within, nor may not be in contact with the surface of the balloon.

Multiple Vibrating-Balloon Device

Referring now to FIG. 7A, in one embodiment, a multiple vibrating-balloon device 700 (only a portion is shown) such as described above may incorporate a single inner lumen 710 such that each of the balloons 702 and their respective elongated body 704 are arranged around the single inner lumen 710, with the inner lumen 710 located away from the outside surface of each balloon 702. In this case, the guidewire 720 may be placed within the valve opening 722, allowing at least one balloon 702 to be in contact with at least one calcified valve leaflet 712 or two or three balloons to be in contact simultaneously with two or three leaflets 712 of the calcified valve for example, allowing for destructuring calcified plaques 718 and nodules 716 sequentially or simultaneously. In alternative embodiments (not illustrated), the inner lumen 710 is concentric with one of the balloons 702, or on the outside surface of one of the balloons 702, or away from the outside surface of each of the other balloons 702. In still a further embodiment, a multiple vibrating-balloon device 700 such as described above may incorporate more than one single inner lumen 710. In yet another embodiment, a multiple vibrating-balloon device 700 such as described above may incorporate one inner lumen 710 per elongated body 704. In another embodiment, a multiple vibrating-balloon device 700 such as described above may incorporate one inner lumen 710 per balloon 702.

Figure 7C:
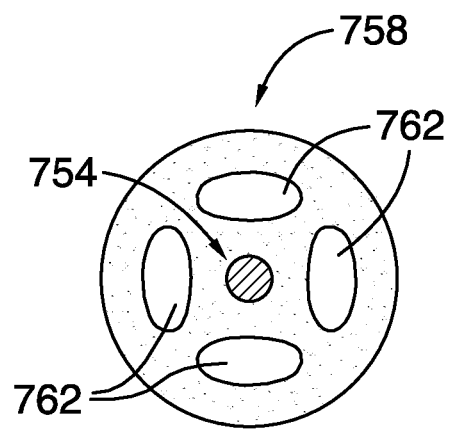
FIG. 7C is a cross-sectional top view of the multi-lobe vibrating-balloon device shown in FIG. 7B in accordance with non-limiting embodiments of the present technology.
Figure 7D:
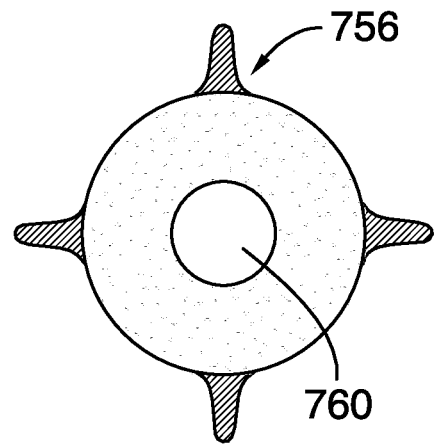
FIG. 7D is a cross-sectional bottom view of the multi-lobe vibrating-balloon device shown in FIG. 7B.

Referring now to FIG. 7B to FIG. 7D, there is shown a vibrating-balloon device 750 provided with a multi-lobe balloon 752 using an elongated body 754, according to another embodiment. In one embodiment, the multi-lobe balloon 752 is pre-shaped using a combination of materials, material thickness and geometrical features for example, as previously described, and is devised to treat simultaneously the three leaflets of the calcified valve 764. As illustrated, the multi-lobe balloon 752 has a distal end 756 and a proximal end 758 and is provided with a single inner blood flow channel 760 at its distal end 756 which splits into four blood flow channels 762 towards its proximal end 758, enabling blood flow from one side of the valve 764 to the other during the treatment. FIG. 7C shows, in cross-sectional view, the proximal end 758 of the balloon 752, with its four blood flow channels 762, while FIG. 7D shows, in cross sectional view, the distal end 756 of the balloon 752, with its single blood flow channel 760. It should be understood that two, four or any other numbers of proximal flow channels 762 may be considered depending on the application.

Triple Balloon

Figure 8B:
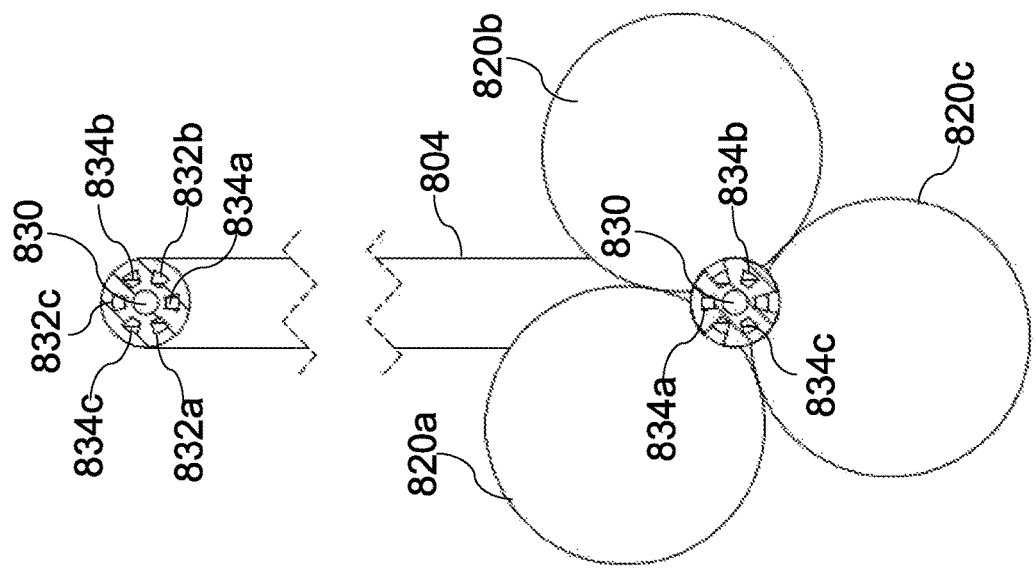
FIG. 8B is a cross-sectional front elevation view of the multi-lobe vibrating-balloon device of FIG. 8A taken along axis BB.
Figure 8A:
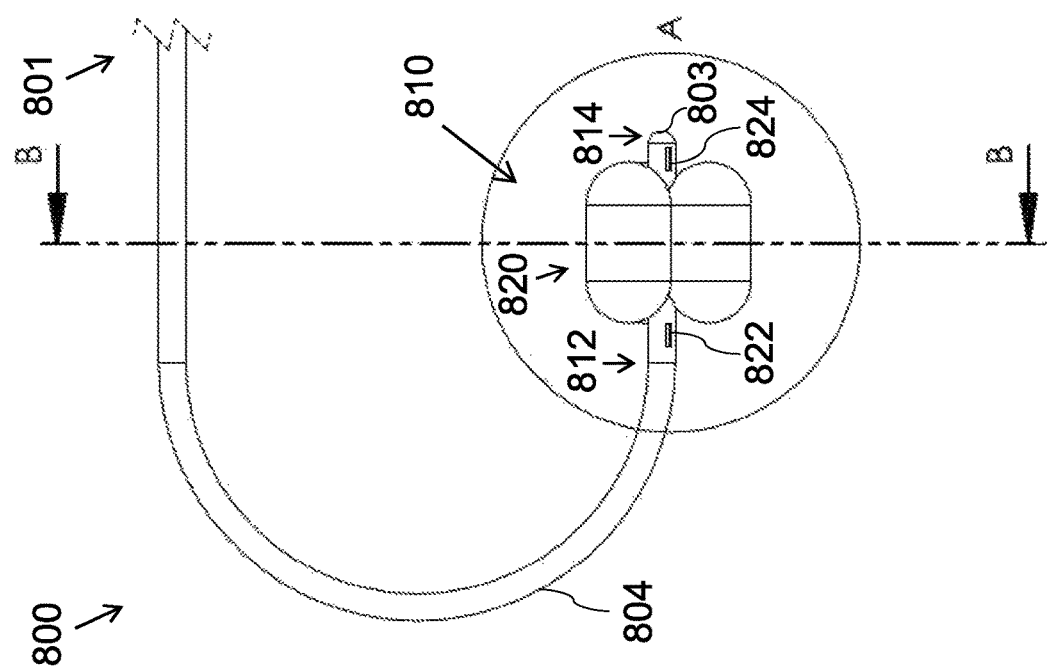
FIG. 8A is a side view taken from the right of a multi-lobe vibrating-balloon device in accordance with non-limiting embodiments of the present technology.
Figure 8C:
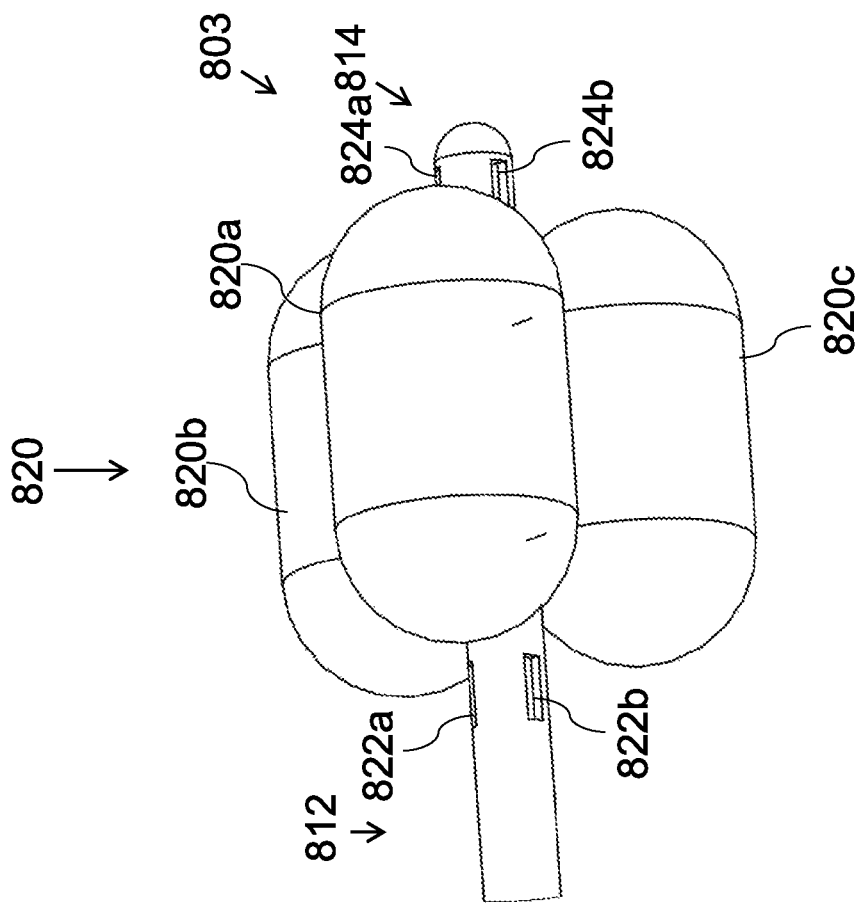
FIG. 8C is a perspective elevation view taken from the right of a tip of the multi-lobe vibrating-balloon device of FIG. 8A

With reference to FIG. 8A to 8C, there is shown another embodiment of a multiple vibrating-balloon device 800.

The second multiple vibrating-balloon device 800 has an elongated body 804 extending between a proximal end 801 and a distal end 803, the elongated body 804 including a tip 810 extending between a proximal tip section 812 and a distal tip section 814 adjacent to the distal end 803.

The elongated body 804 comprises an inner lumen 830 shaped and sized for insertion of a wire therein, three balloon lumens 832 and three blood flow lumens 834a, 834b and 834c.

The second multiple vibrating-balloon device 800 has three inflatable balloons 820: a first inflatable balloon 820a, a second inflatable balloon 820b and a third inflatable balloon 820c located at an outer surface of the elongated body 804 between the proximal tip section 812 and the distal tip section 814 at different radial locations around the circumference of the elongated body 804. In the illustrated embodiment, each of the first inflatable balloon 820a, the second inflatable balloon 820b and the third inflatable balloon 820c are positioned at 120 degrees of each other radially about the longitudinal axis of the elongated body 804 such that the three balloons 820 address all three aortic valve leaflets. However, the person skilled in the art would understand that the radial position of the balloons 820 may vary.

The elongated body 804 defines a set of proximal longitudinal openings 822 located adjacent to the proximal tip section 812 before the three inflatable balloons 820 and a set of distal longitudinal openings 824 located adjacent the distal tip section 814, the second longitudinal opening 824 being located after the three inflatable balloons 820.

The set of longitudinal openings 822 comprises three longitudinal openings (only two visible in FIG. 8C): a first longitudinal opening 822a, a second longitudinal opening 822b and a third longitudinal opening (not shown). The set of distal openings 824 comprises three distal openings (only two visible in FIG. 8C): a first distal opening 824a, a second distal opening 824b and a third distal opening (not shown). It should be understood that there may be at least one longitudinal opening in the set of longitudinal openings 822 and at least one longitudinal opening.

The set of longitudinal openings 822 is connected to the set of distal openings 824 via the three blood flow lumens 834 to enable blood flow. The first blood flow lumen 834a connects the first longitudinal opening 822a to the first distal opening 824a, the second blood flow lumen 834b connects the second longitudinal opening 822b and the second distal opening 824b, and the third blood flow lumen 834c connects the third longitudinal opening (not shown) to the third distal opening (not shown). It should be understood that number of blood flow lumens is equal to the number of pairs of longitudinal and distal openings.

The three balloon lumens 832 comprise a first balloon lumen 832a in fluid communication with the first inflatable balloon 820a, a second balloon lumen 832b in fluid communication with the second inflatable balloon 820b, and a third balloon lumen 832c in fluid communication with the third inflatable balloon 820c. In one embodiment, each of the first balloon lumen 832a, the second balloon lumen 832b and the third balloon lumen 832c is connected to a respective fluid source (not shown) at the proximal end 801 which enables to independently and selectively inflate and deflate each of the first inflatable balloon 820a, the second inflatable balloon 820b and the third inflatable balloon 820c, i.e. one, two or three of the three inflatable balloons 820 may be inflated depending on the application. It should be understood that in another embodiment, a single fluid source may be connected to the three inflatable balloons 820 for inflation thereof.

As best seen in FIG. 8C, each of the first inflatable balloon 820a, the second inflatable balloon 820b and the third inflatable balloon 820c are provided with an ellipsoid shape, but this does not need to be so in every embodiment of the present technology, i.e. the first inflatable balloon 820a, the second inflatable balloon 820b and the third inflatable balloon 820c may have another shape or each have a different shape.

The second multiple vibrating-balloon device 800 is provided with pressure sensor (not shown) inside at least one of the first inflatable balloon 820a, the second inflatable balloon 820b and the third inflatable balloon 820c for monitoring time-varying pressure.

In one embodiment, the above-described vibrating-balloon device may be further provided with at least one sensor for monitoring the filing of the balloon with fluid and the vibrations of the balloon. It should be understood that when a vibrating-balloon device comprises more than one balloon, more than one sensor may be included into the vibrating-balloon device.

For example, the vibrating-balloon device may comprise a pressure sensor for measuring the pressure of the fluid and determine the filing state/level of the balloon and/or the vibrations of the balloon. For example, the pressure sensor may be positioned within the balloon and secured to the elongated body.

It should be understood that any adequate sensor for monitoring the filing state/level of the balloon and/or the vibrations of the balloon may be used. For example, an impedance sensor may be used for measuring the impedance of the fluid and determine therefrom the pressure force of the inflated balloon with the targeted tissue where the vibration will be applied. In this case, the vibrating-balloon device may be provided with at least two electrodes to measure the impedance and the electrodes may be positioned within the balloon and secured to the elongated body.

Rotating Tip

With reference to FIG. 9A and FIG. 9B, there is shown a vibrating-balloon-device 900 accordance with non-limiting embodiments of the present technology.

The vibrating-balloon-device 900 has an elongated tubular body having a proximal end 901 and a distal end 903. The elongated tubular body includes a tip section 910 extending between a proximal tip section 912 and a distal tip section 914.

The vibrating-balloon-device 900 includes an inflatable balloon 920 located within the tip section 910, between the proximal tip section 912 and the distal tip section 914.

The proximal end 901 of the vibrating-balloon-device 900 is operatively connected to a steering handle 990. The steering handle 990 is operatively connectable to a vibration source (not shown) for generating vibrations at the distal end 903 of the vibrating-balloon device.

In this embodiment, the elongated tubular body includes a tip 901 extending between a proximal tip section 912 and a distal lip section 914, where the tip 910 includes an inflatable balloon 920 located between the proximal tip section 912 and the distal tip section 914 inside or integral with the elongated tubular body. When in the inflated state, as shown in FIG. 91B, the inflatable balloon 920 is bell-shaped. It is contemplated that the inflatable balloon 920 may have a semi-circular or ellipsoidal shape.

The elongated tubular body comprises a lumen 916 in fluid communication with the inflatable balloon 920 and extending between the proximal tip section 912 and the distal tip section 914, the lumen 916 defining a fluid path which enables to enable inflate and deflate the inflatable balloon 920.

The elongated tubular body is generally made from a flexible material such that the tip 910 follows the shape of the inflatable balloon 920 when the inflatable balloon 920 is in an inflated state, as shown in FIG. 913, and returns to a substantially tubular shape when the inflatable balloon 920 is in a deflated state (not shown).

The elongated tubular body comprises a rotation arm 918 extending from the proximal end 901 to the distal end 903 inside the inflatable balloon 920. In one embodiment, the rotation arm 918 is inserted into at least a portion of the rotatable element 934 of the inflatable balloon 920. In one embodiment, the rotation arm 918 is also made of a flexible material such that it follows the shape of the outer surface of the inflatable balloon 920 when it is inflated and deflated. In one embodiment, the rotation arm 918 has an asymmetric shape.

The rotation arm 918 is rotatably coupled to a first rotative element 932 at the proximal tip section 912 of the tip 910 and is rotatably coupled to a second rotative element 934 at the distal tip section 914. In one embodiment, the second rotative element 934 and/or distal tip section 914 is/are fixed to the distal end 903 of the elongated tubular body. In one embodiment, the first rotative element 932 and the second rotative element 934 are bearings.

The first rotative element 932 and the second rotative element 934 enable rotation of the rotation arm 918 about its longitudinal axis. In one embodiment, rotation of the rotation arm 918 is controlled via the steering handle 990 connected to a rotation source (not shown). The rotation source or control unit (not shown) is operable to provide rotational energy to the rotation arm 918 via the steering handle 990, which causes the rotation arm 918 to rotates about the longitudinal axis of the elongated flexible body 904 and thereby causes rotation and vibration of the inflatable balloon 920 and the surface of the tip 910 of the elongated tubular body 904.

In-use, the vibrating-balloon-device 900 may be positioned in close proximity with body tissues including the calcified structures when the inflatable balloon 920 is in a deflated state and the rotation arm 918 may be rotated along its longitudinal axis such that the inflatable balloon 920 can be positioned in a radial direction towards a calcified tissue region and the inflatable balloon 920 may be inflated. The rotation source is activated to cause rotational motion of the rotation arm 918, thereby causing rotation and vibration of the inflatable balloon 920 such that the tip 910 transmits mechanical vibration to the calcified tissue region while also allowing blood flowing due to the inflatable balloon 920 and the tip 910 not extending in all radial directions.

Pressure Source

In one embodiment, the balloon device is connectable to a single source of fluid for selectively inflating and deflating the balloon and varying the pressure of the fluid within the balloon once inflated. In this case, the source of fluid may be referred to as an inflation and vibration source of fluid or an oscillatory pressure source of fluid. The same source of fluid is used for both inflating the balloon and oscillatory varying the pressure of the fluid within the balloon so as to create vibrations of the wall of the balloon.

Referring back to FIG. 2A, in another embodiment, the balloon device is connectable to two distinct sources of fluid: a static pressure source and a dynamic pressure source. The static pressure source is connectable to one of the two inlets of the connector 408 and the dynamic pressure source is connectable to the other inlet of the connector 408. The static pressure source is used to inject into the balloon a fluid having a baseline slowly varying balloon inflation pressure and the dynamic pressure source is used to inject a fluid having a more rapidly time-varying balloon pressure, the two pressures being independently controlled. It should be understood that the static pressure source and the dynamic pressure source may be combined together in a single pressure source, keeping the two pressures independently controlled, providing simultaneous steady and time-varying balloon inflation pressures.

In one embodiment, the source of fluid is provided with a pressure sensor (not shown) for monitoring the time-varying pressure of the injected fluid. The pressure sensor has sufficient range, resolution and time-response to adequately capture the time-varying pressure produced by source of fluid. The pressure sensor may be used to simply display the time-varying pressure produced by the source of fluid and it may also be used as part of a closed-loop control system used to prescribe the time-varying pressure produced by the source of fluid.

In one embodiment, the source of fluid uses at least one piston-type pump or compressor where a piston travels axially within a cylinder, thereby changing the volume and pressure within the cylinder. The piston motion may be actuated via a solenoid, a linear electric motor, a pneumatic cylinder, a hydraulic cylinder or a slider-crank mechanism driven by a rotary electric, pneumatic or hydraulic motor. Alternatively, the source of fluid may use a rotary pump or compressor where the impeller may be of the axial, radial or mixed flow configuration. The skilled addressee will appreciate that various other arrangements may be considered.

Pressure Sensor

In one embodiment, the inflatable balloons 402, 502, 512, 602, 702, 752, 820, 920 previously described may also comprise at least one pressure sensor (not shown) for monitoring the pressure applied to the tissue structure and oscillating pressure within the inflatable balloons during vibrating energy application. The pressure sensor has sufficient range, resolution and time-response to adequately capture the time-varying pressure within the inflatable balloon. The pressure sensor may be used to display the time-varying pressure within the inflatable balloon and may also be used as part of a closed-loop control system used to prescribe the time-varying pressure within the balloon. The pressure sensor may also be used to monitor the pressure applied to the tissue structure. Electrical leads for powering and reading the output of the balloon pressure sensor may run on the inside surface, the outside surface or within the elongated body. Alternatively, the output of the balloon pressure sensor may be read wirelessly.

As previously mentioned, the overall pressure "p" produced by the source of fluid may be obtained as a combination of a static pressure "ps" and a dynamic pressure "pd", where p, ps and pd are functions of time "t" such that: $p(t)=ps(t)+pd(t)$. Before treatment of the calcified tissue, both the static and dynamic pressures correspond to the local atmospheric pressure such that the so-called gauge static and dynamic pressures are zero.

Figure 10A:
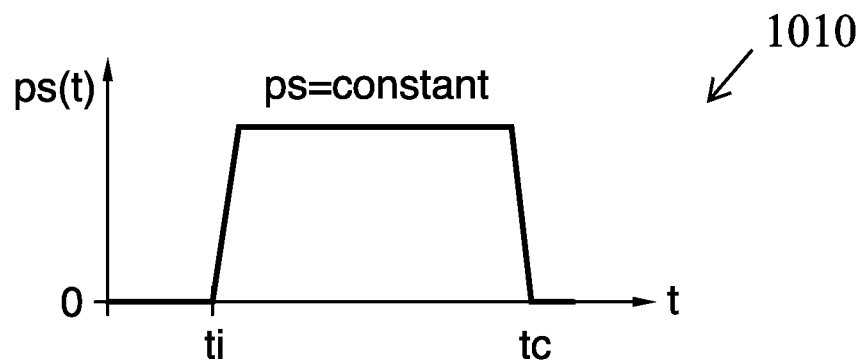
FIG. 10A to 10C each illustrates a plot of static pressure vs time used for inflating a balloon of a vibrating-balloon device in accordance with non-limiting embodiments of the present technology.

With reference to FIG. 10A, a plot 1010 of pressure in function of time is shown, where the static pressure ps(t) is maintained constant in time after balloon inflation at t=ti. In another embodiment, the static pressure is zero (i.e., atmospheric pressure) at all times, such that ps(t)=0.

Figure 10B:
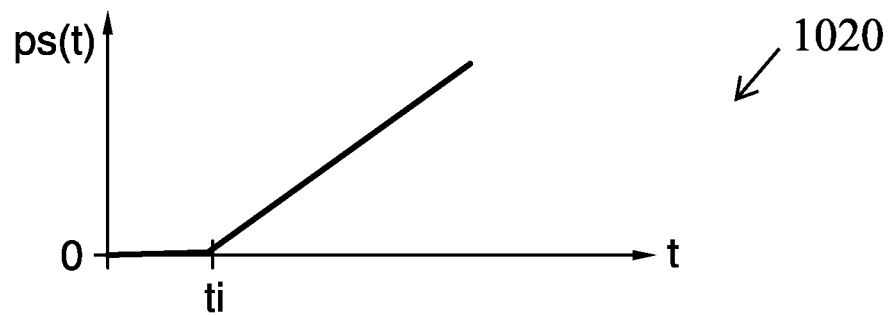

With reference to FIG. 10B, a plot 1020 of pressure in function of time is shown, where the static pressure increases in time after balloon inflation at t=ti. This increase in time may be linear, parabolic or any monotonic function of time.

Figure 10C:
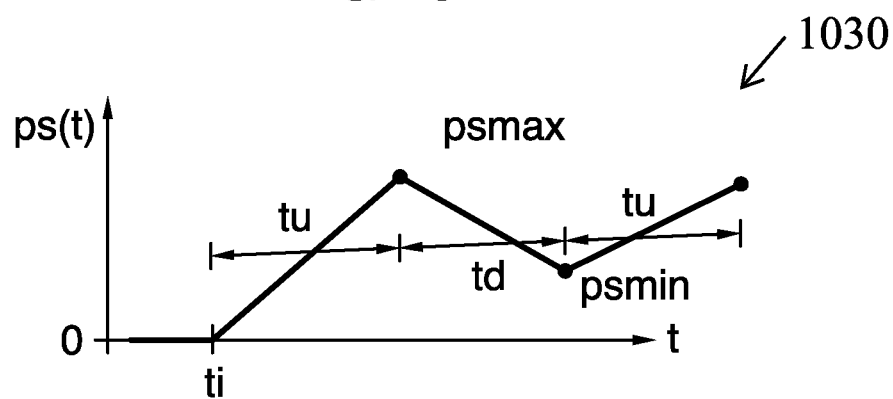

With reference to FIG. 10C, a plot 1030 of pressure in function of time is shown, where the static pressure successively increases and decreases in time after balloon inflation at t=ti, reaching a maximum static pressure psmax after a time interval to and a minimum pressure psmin after a time interval td, where the variation in static pressure may be cyclically repeated throughout the treatment. The static pressure is reduced back to zero (i.e., at atmospheric pressure) after completion of treatment at t=tc, as shown in FIG. 10A for example.

Figure 10D:
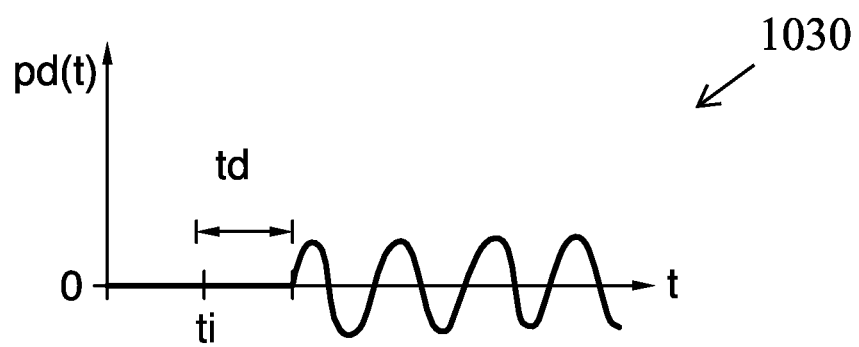
FIG. 10D to 10E each illustrates a plot of dynamic pressure in function of time used to vibrate a balloon of a vibrating-balloon device in accordance with non-limiting embodiments of the present technology.
Figure 10E:
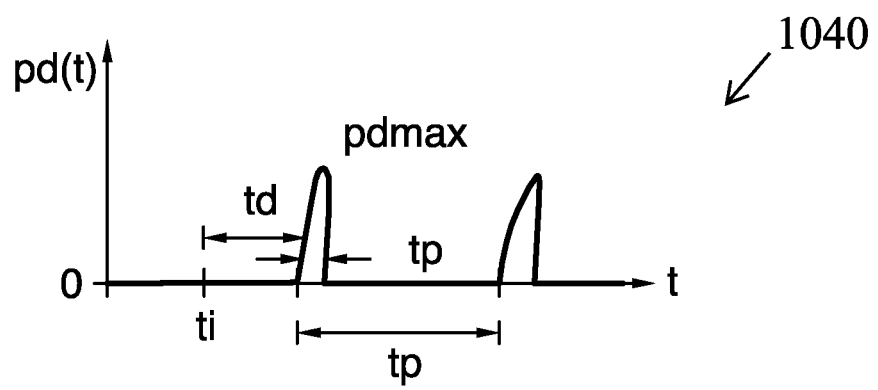

With reference to FIG. 10D, a plot 1040 of pressure in function of time is shown in, where the dynamic pressure pd(t) varies cyclically in time starting at a time interval td after balloon inflation at t=ti. In one embodiment, td=0, while in another embodiment td>0. In one embodiment, the cyclic variation of dynamic pressure in time may be a sinusoidal wave, as illustrated, while in another embodiment, the cyclic variation of dynamic pressure in time may be a triangular or square wave as non-limitative examples.

In one embodiment, the cyclic variation of dynamic pressure in time may have a constant amplitude, while in another embodiment, the cyclic variation of dynamic pressure in time may have an amplitude which increases monotonically in time. In one embodiment, the cyclic variations of dynamic pressure in time may have a constant period, while in another embodiment, the cyclic variation of dynamic pressure in time may have a period which monotonically increases or decreases in time. In one embodiment, the cyclic variation of dynamic pressure in time may be a chirp. In another embodiment, the cyclic variation of dynamic pressure in time may comprise both a change in amplitude and period/frequency. In one embodiment, the cyclic variation of dynamic pressure in time may be a combination of multiple sinusoidal waves, each having a different period/frequency and amplitude.

In one embodiment, the dynamic pressure pd(t) is a pulse of temporal width Δtp and pressure amplitude pdmax, applied a time delay td after balloon inflation at t=ti, as shown in FIG. 8E. The pressure pulse may be repeated at an interval tp which may be constant or vary in time, and the amplitude pdmax of the pulse may be constant or vary in time. In another embodiment, the amplitude of the pressure pulse pdmax may be negative or it may be alternating between positive and negative from one pulse to the next.

In one embodiment, the combination of static and dynamic pressures may be selected to induce mechanical vibration resonance of the vibrating-balloon device at one of its resonant frequencies, which may depend on the geometrical properties (for example, length, inner diameter and volume) and the mechanical properties (for example, flexural, torsional and circumferential stiffness) and surroundings of each component of the device. The resonant frequencies of the vibrating-balloon device may comprise: i) flexural, torsional and shear modes of the elongated body; ii) longitudinal and radial modes for the fluid motion within the elongated body; iii) flexural, torsional and shear modes of the balloon; iv) longitudinal, radial, circumferential and azimuthal modes for the fluid motion within the balloon; v) resonator modes for the balloon coupled with the elongated body or any combinations and couplings of these. Inducing resonance of the vibrating-balloon device may increase the amplitude of the balloon mechanical vibrations which may promote more efficient cracking, breaking and/or destructuring of the calcified structure present on or within a diseased valve. The resonant frequency or frequencies of the device may be identified a priori for a given vibrating-balloon device, either experimentally, analytically or using a computer model, these approaches being well known in the field of vibration analysis. The resonant frequency or frequencies of the vibrating-balloon device may also be identified in situ during treatment by scanning p(t) through an appropriate range of frequencies and simultaneously measuring the pressure source and/or balloon pressure with the aforementioned pressure sensors to detect resonance. Once the appropriate resonant frequencies are identified, either a priori or in situ, they may be used to specify the time-varying pressure p(t) from the pressure source to promote more efficient treatment.

In one embodiment, the static and dynamic pressures may be selected to induce mechanical vibration resonance of one of the calcified valve structures at one of its resonant frequencies which may depend on the geometrical properties, the mechanical properties and the surroundings of the one calcified structure. Inducing resonance of one of the calcified valve structures may increase the amplitude of the mechanical vibrations of the one calcified valve structure which may promote more efficient cracking, breaking and/or destructuring of the one calcified scaffolding structure. Since a diseased calcified valve leaflet may comprise more than one calcified structure, each potentially having its own resonant frequencies, treatment may also be accomplished in an open-loop approach by imposing a prescribed time-varying pressure whose frequency varies in time such that each calcified structure is eventually exposed to its resonant frequency. Treatment may also be accomplished in a closed-loop approach where the resonant frequency or frequencies of the one calcified structure may be identified in situ during treatment by scanning p(t) through the appropriate range of frequencies and simultaneously measuring the pressure source and/or balloon pressure with the aforementioned pressure sensors to detect resonance. Once the appropriate resonant frequencies of the one calcified structure are identified in situ, they may be used to specify the time-varying pressure p(t) from the pressure source to promote more efficient treatment of the one calcified structure. This procedure may be repeated for each calcified structure.

In another embodiment, the time-varying pressure p(t) from the pressure source may combine signals aimed at inducing simultaneous resonance of both the vibrating-balloon device and at least one calcified structure present on or within a diseased calcified valve leaflet.

The vibrating-balloon device described above may also be used to treat other valves where calcified structures are problematic, such as the mitral valve. The vibrating-balloon device described above may also be used to treat other instances where calcified structures are problematic, such as in peripheral and coronary artery disease. In this case, the vibrating-balloon device may be inserted in an arterial lumen and inflated with a time-varying pressure to promote cracking, breaking and/or destructuring of the calcified scaffolding structures within the diseased artery wall.

Prototype Experiments

Figure 11A:
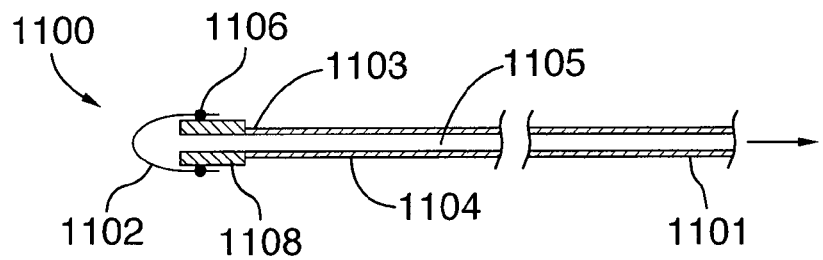
FIG. 11A is a schematic diagram of a cross-sectional elevation view of a prototype of a vibrating-balloon device in accordance with non-limiting embodiments of the present technology.

The performance of a prototype vibrating-balloon device was tested on ex-vivo calcified aortic valves obtained from cadavers. As shown in FIG. 11A, the vibrating-balloon prototype device 1100 has an elongated body 1104 having a proximal end 1101 and a distal end 1103 and defining a fluid path 1105 therebetween. The vibrating-balloon prototype device 1100 has a rigid tube 1108 mounted to the distal end 1103 of the elongated body 1104 where the rigid tube 1108 is secured to the distal end 1103 of the elongated body 1104. The vibrating-balloon prototype device 1100 also has an inflatable balloon 1102 mounted over the rigid tube 1108. In the illustrated embodiment, the inflatable balloon 1102 is in an inflated state and is secured to the rigid tube 1108 with a clamp 1106. As a non-limiting example, the vibrating-balloon prototype device 1100, the elongated body 1104 may have a length of 75 cm and an internal diameter of 3.175 mm. The rigid tube 1108 may have an external diameter of 10 mm and be 10 mm long. The balloon 1102 may be made from a 0.4 mm thick 70 A durometer neoprene membrane. The clamp 1106 is made from a ductile steel wire.

Figure 11B:
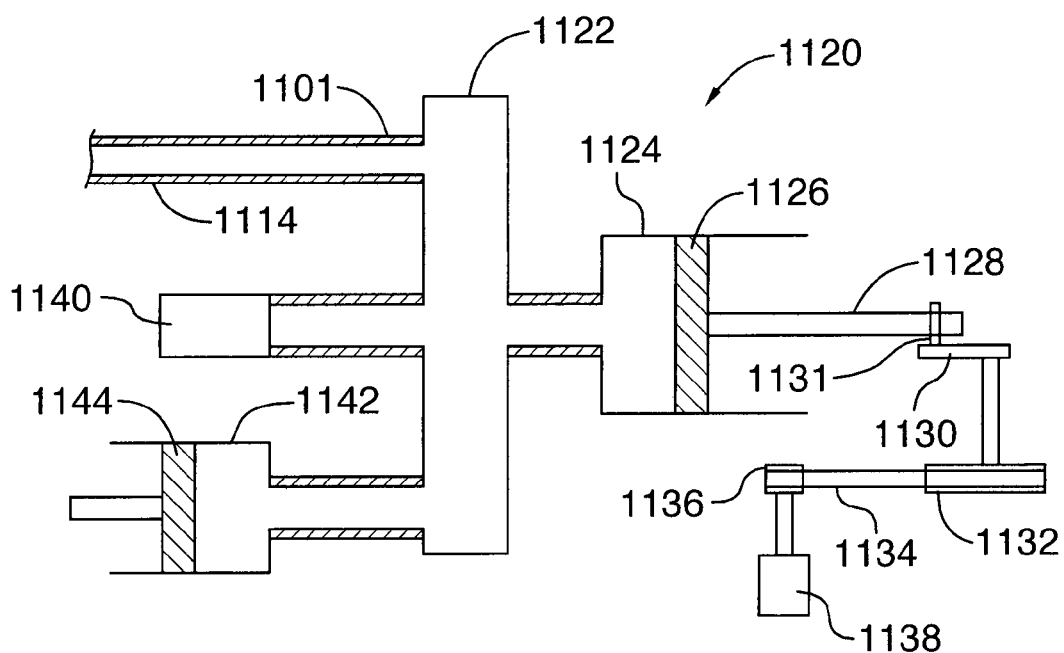
FIG. 11B is a schematic diagram of a cross-sectional view of an inflation and vibration source connectable to the prototype of FIG. 11A in accordance with non-limiting embodiments of the present technology.

The vibrating-balloon prototype device 1100 also has an source of fluid 1120 operatively connected to the proximal end 1101 of the elongated body 1104. As shown in FIG. 11B, the source of fluid 1120 comprises a piston-type pump where a piston 1126 travels axially within a cylinder 1124, thereby changing the volume and pressure within the cylinder. The piston motion is actuated via a slider-crank mechanism, where the crank arm 1128 is connected to a rotating arm 1130 which is driven by a rotary electric motor 1138 via a large pulley 1132, a belt 1134 and a small pulley 1136 connected to a rotary electric motor 1138 (e.g., model GoolRc S3674). The attachment point 1131 of the crank arm 1128 to the rotating arm 1130 may be moved to change the cylinder displacement from 1 to 7 cc. The electrical signals to vary the rotational speed of the electric motor are provided by a controller such as an Arduino Mega2560 controller (not shown).

The cylinder 1124 is fluidly connected to a manifold 1122 allowing for simultaneously connecting the proximal end 1101 of the elongated body 1104, a pressure sensor 1140 (e.g., Honeywell Model PX2AN1XX050PAAAX) and a syringe 1142. The syringe 1142 is equipped with a plunger 1144 whose axial position is adjusted to maintain a constant static pressure ps.

Figure 11C:
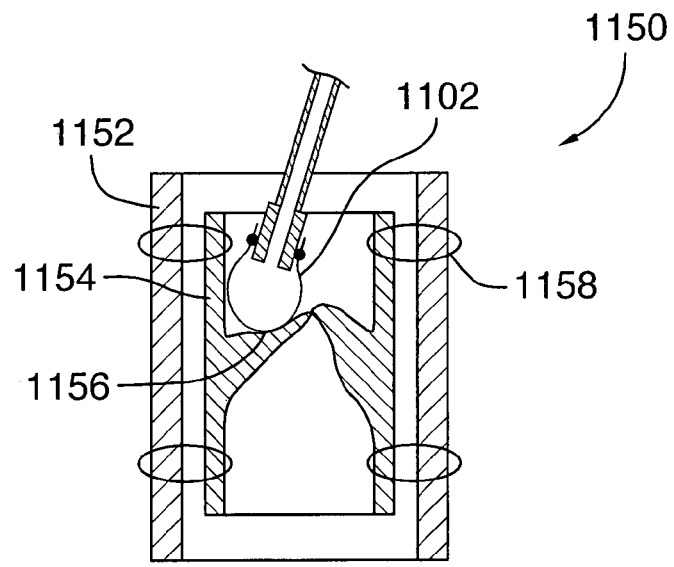
FIG. 11C is a schematic diagram of a test setup used with the prototype of FIG. 11A in accordance with non-limiting embodiments of the present technology.

FIG. 11C shows the test setup 1150 which includes a rubber tube 1152, having an internal diameter of 25.4 mm and a length of 63.5 mm, used to hold in place a cadaveric calcified valve 1154. The valve 1154 is secured to the rubber tube 1152 using nylon threads 1158 sewn into both the valve 1154 and the tube 1152. The test setup 1150 is immersed in a 0.9% saline bath maintained at 37° C.

Figure 11D:
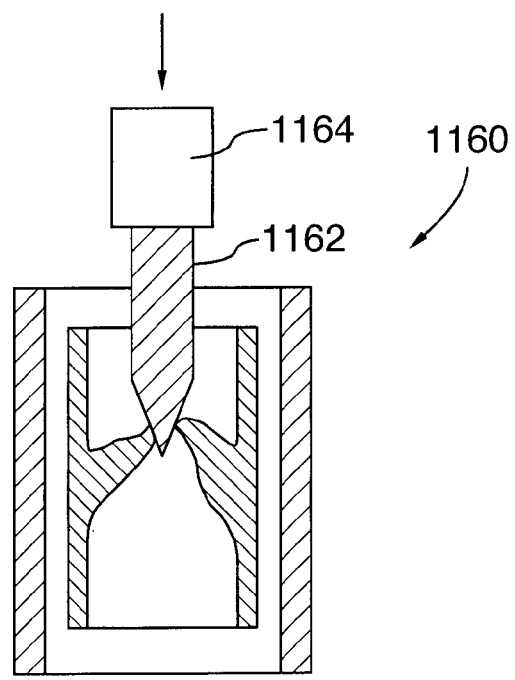
FIG. 11D is a schematic diagram of another test setup used with the prototype of FIG. 11A in accordance with non-limiting embodiments of the present technology.

As shown in FIG. 11D, another test setup 1160 is used to measure the rigidity of the valve by monitoring the force-displacement history of a conical plunger 1162 inserted into the valve. The plunger 1162 may have a diameter of 12.7 mm, 15.8 mm or 19 mm and the conical tip of the plunger has a solid angle of 45 degrees. The plunger is moved into the valve axis using a force tester such as a Mark 10 ESM303 single-column force tester (not shown) with the force and displacement simultaneously measured using a force gauge 1164 such as a Series 5 force gauge.

To perform a test, the first step is measuring the mechanical rigidity of the valve using the setup 1160 of FIG. 11D prior to treatment with the vibrating-balloon prototype device 800 to assess the baseline rigidity characteristics of a particular valve. The second step is inflating the balloon 1102 to a constant static pressure ps, using the syringe 1142 and plunger 1144, and placing the balloon 1102 in contact with one of the valve leaflets 1156, as shown in FIG. 11C. A treatment is then performed by oscillating the balloon 1102 at a low frequency, usually 1 Hz. Then the rigidity of the valve is measured a second time with the setup 1160 of FIG. 11D. The third step is inflating the balloon 1102 to a constant static pressure ps, using the syringe 1142 and plunger 1144, and placing the balloon 1102 in contact with a valve leaflet 1156, as shown in FIG. 11C. A treatment is then performed by oscillating the balloon 1102 at various frequencies, typically swept from 20 Hz to 100 Hz, against each of the valve leaflets in sequence. The rigidity of, the valve is then measured a final time using the setup 1160 of FIG. 11D.

Figure 11E:
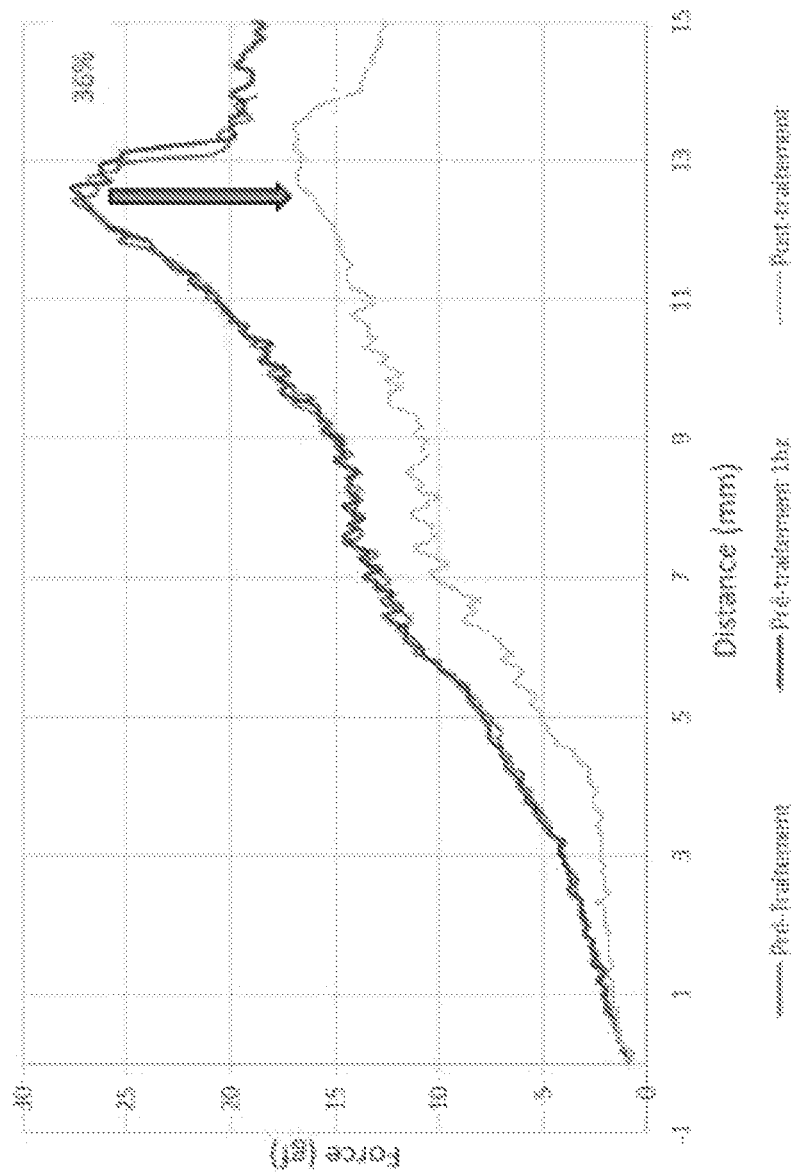
FIG. 11E is a plot of force in function of distance obtained

With reference to FIG. 11E, there is shown a plot 1190 of force in function of time, which is a non-limiting example of a test performed with the test sequence described herein above. The graph shows the force displacement profile of a valve before treatment, after 1 Hz treatment and after 20-100 Hz sweep treatment. For this test the static pressure ps was 15 psi and the dynamic pressure was sinusoidally varying with an amplitude of +/−2.5 psi using a cylinder displacement of 5 cc. This caused the balloon diameter to oscillate between a minimum diameter of 13.5 mm and a maximum diameter of 15.2 mm. The 20-100 Hz frequency sweep was taking place over a twelve-minute time duration. The graph of FIG. 9E shows that the treatment at 1 Hz did not modify the rigidity of the valve as the force-displacement curve after the 1 Hz treatment is practically identical to the pre-treatment curve. The results also show how the valve was made more flexible, i.e., less rigid, by the 20-100 Hz treatment, as for a plunger displacement of 13 mm the force required was reduced from about 27 gf (grams-force) to 17 gf, a reduction of nearly 40%.

Thus, using an oscillating balloon device as described above enables making calcified heart valves more flexible, especially using a combination of static and dynamic pressures.

Energy Sources for Vibration

While in the above description, the described vibrating-balloon device use a source of fluid for generating vibrations within the balloon, it should be understood that any adequate method/system for vibrating the balloon once inflated may be used. In the following there is described exemplary vibrating-balloon devices for which the balloon is vibrated using vibration source other than the source of fluid. In this case, once the balloon has been inflated using the source of fluid, a distinct source of vibrations is actuated to generate mechanical waves into the fluid contained into the balloon and thereby vibrate the balloon.

Figure 12A:
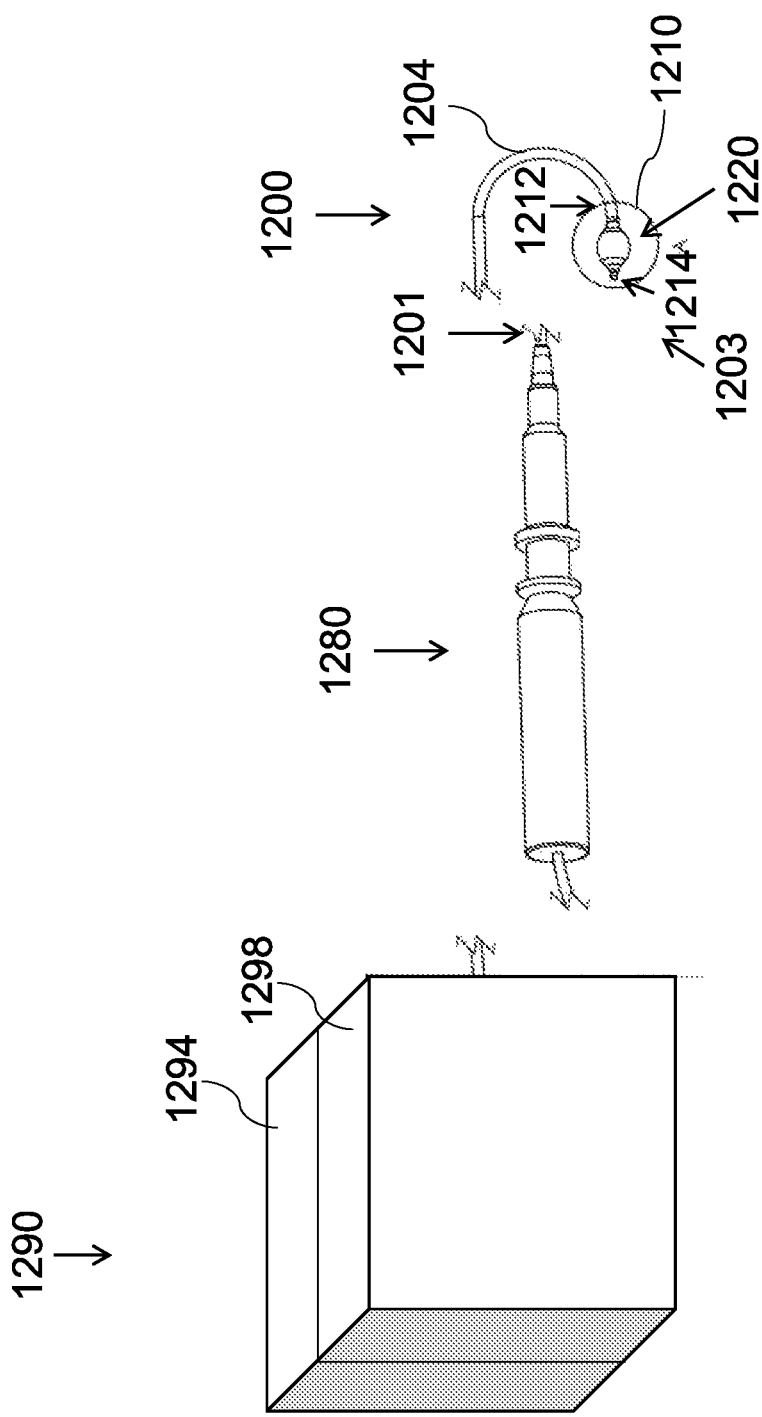
FIG. 12A is a schematic perspective elevation view of vibrating-balloon device connected to an inflation and vibration source in accordance with non-limiting embodiments of the present technology.

With reference to FIG. 12A there is shown a vibrating-balloon device 1200 in accordance with non-limiting embodiments of the present technology.

The vibrating-balloon device 1200 comprises an elongated body 1204 extending between a proximal end 1201 and a longitudinal end 1203. The elongated body 1204 has a tip 1210 extending between proximal tip section 1212 and a distal tip section 1214.

The proximal end 1201 is connected to a vibration and inflation source 1290 via a steering handle 1280 to be used to manipulate the vibrating-balloon device 1200. The vibration and inflation source 1290 comprises an inflation source 1294 and a vibration source 1298.

In one embodiment, a section of the elongated body 1204 is deflectable. It should be understood that any adequate system for deflecting a section of the elongated body 1204 may be used. In one embodiment, a cable running from the steering handle 1280 and secured to the section of the elongated body 1204 to be deflected may present and the, elongated body 1204 may be deflected by pulling on the cable. In one embodiment, the section of the elongated body 1204 may be mechanically deflected from a zero to a maximum of 270° curve deflection versus elongated body straight axis. The proximal part of the elongated body is in a substantially straight shape (not shown), as depicted in FIG. 12A.

In the illustrated embodiment, the inflation source 1294 is operable to inflate the inflatable balloon 1220 with an electrically conductive fluid. As a non-limiting example, the conductive fluid may be a 0.9% NaCl Solution.

The vibration source 1298 is operable to induce mechanical vibrations at the outer surface of the inflatable balloon 1220 via the conductive fluid via different sources of energy.

In one embodiment, the elongated body 1204 comprises a sensor 1240 located within the tip for determining a filling status of conductive fluid in the internal balloon 1220 to avoid applying the vibration source 1298 when the internal balloon 1220 does not contain an amount of fluid below a predetermined threshold. Additionally in order to monitor the temperature inside the balloon, the balloon comprises a temperature sensor 1240 for determining the temperature of the conductive fluid inside the balloon.

Different embodiments for inducing the mechanical vibrations at the outer surface of the tip 1220 will now be described with reference to FIG. 12B to FIG. 12D

Figure 12B:
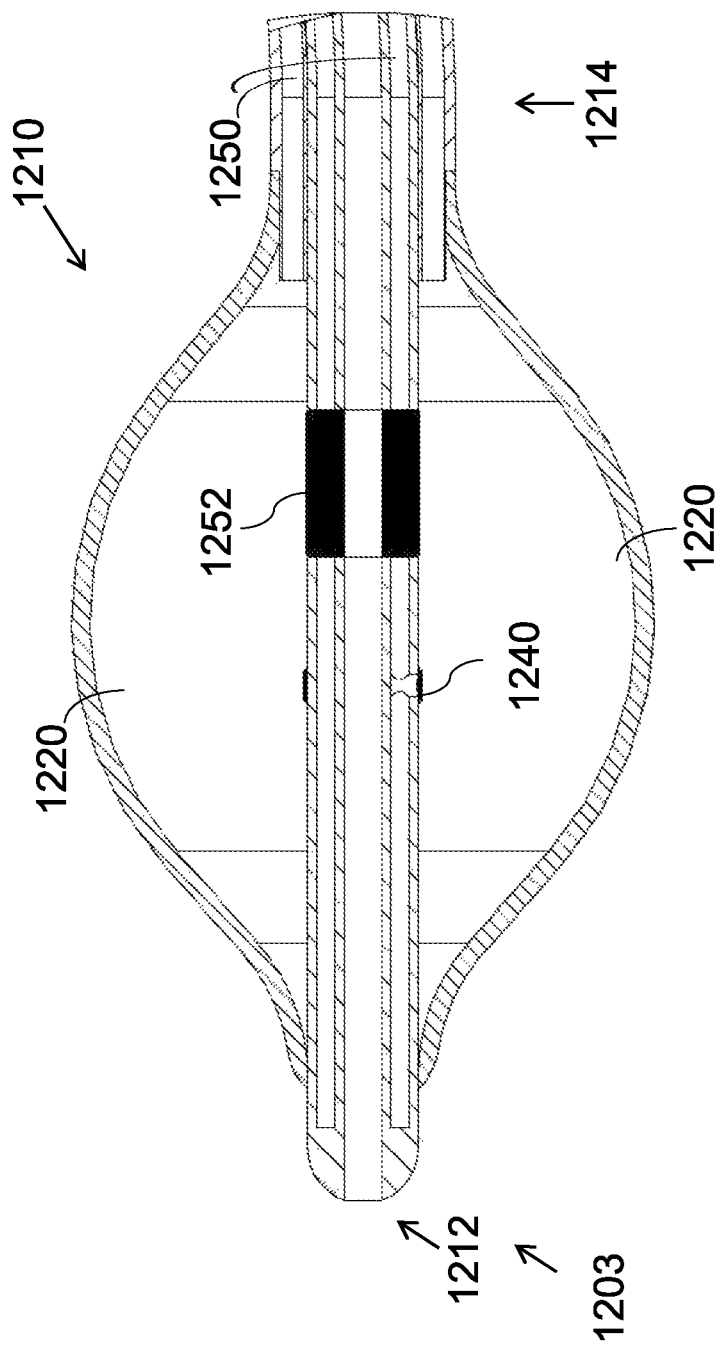
FIG. 12B is a cross-sectional elevation view of non-limiting embodiment of a tip of the device of FIG. 12A.

With reference to FIG. 12B, the vibration source 1298 is a laser coupled to a fiber 1250, the fiber 1250 located within the elongated body 204 and extending between the proximal end 1201 and the distal end 1203. The balloon 1220 comprises a transmitter 1252 coupled to the fiber and located within the tip 1210. In alternative embodiments, there may be more than one transmitter 1252 coupled to the fiber.

The transmitter 1252 is operable to receive laser pulses from the vibration source 1298, i.e. the laser, and generate high energy mechanical pulses in the conductive liquid, thereby inducing mechanical vibrations at the outer surface of the inflatable balloon 1220 for destructuration of the calcified structures.

Figure 12C:
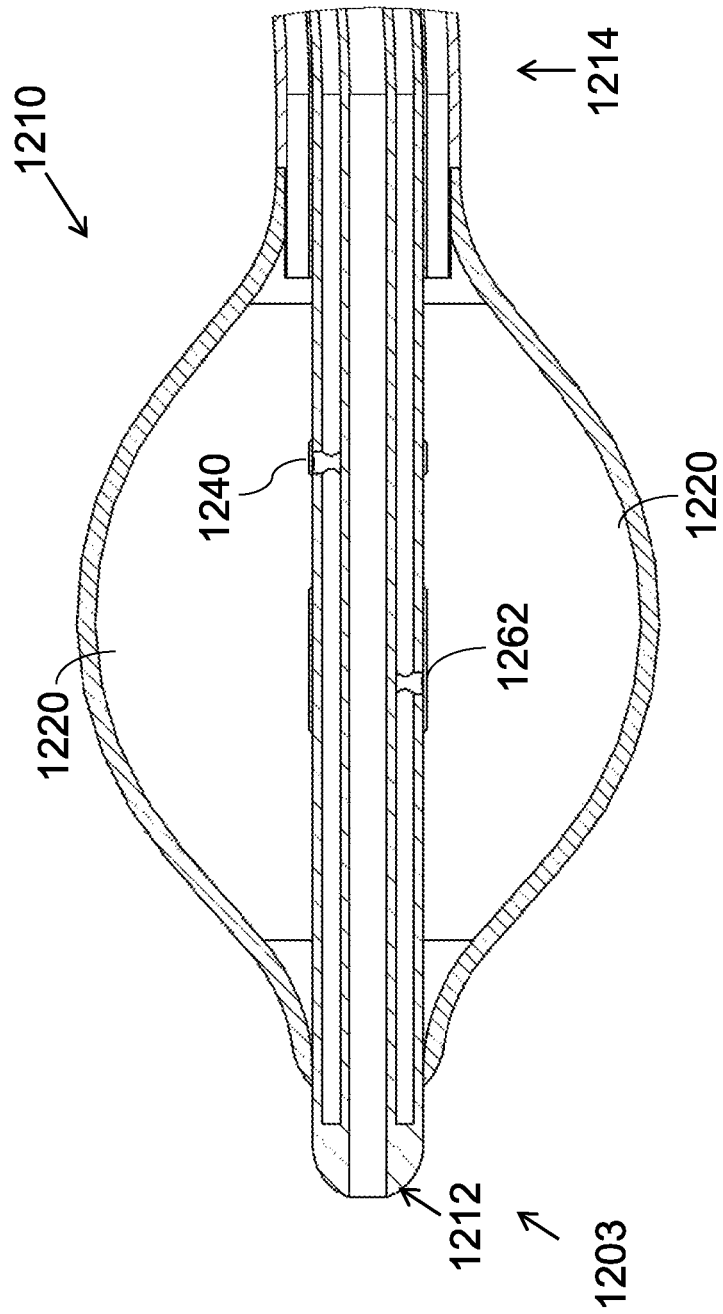
FIG. 12C is a cross-sectional elevation view of non-limiting embodiment of a tip of the device of FIG. 12A.

With reference to FIG. 12C, the vibration source 1298 is piezoelectric unit connected to a piezoelectric element 1262 located within the tip 1210. In an alternative embodiment, there may be more than one piezoelectric element 1262 connected to the vibration source 1298.

The piezoelectric element 1262 is operable to receive electrical power from the vibration source 1298 and generate high energy lithotripter and/or acoustic pulses which induce vibrating energy loaded waves in the conductive liquid thereby inducing mechanical vibrations at the outer surface of the inflatable balloon 1220 for destructuration of the calcified structures.

Figure 12D:
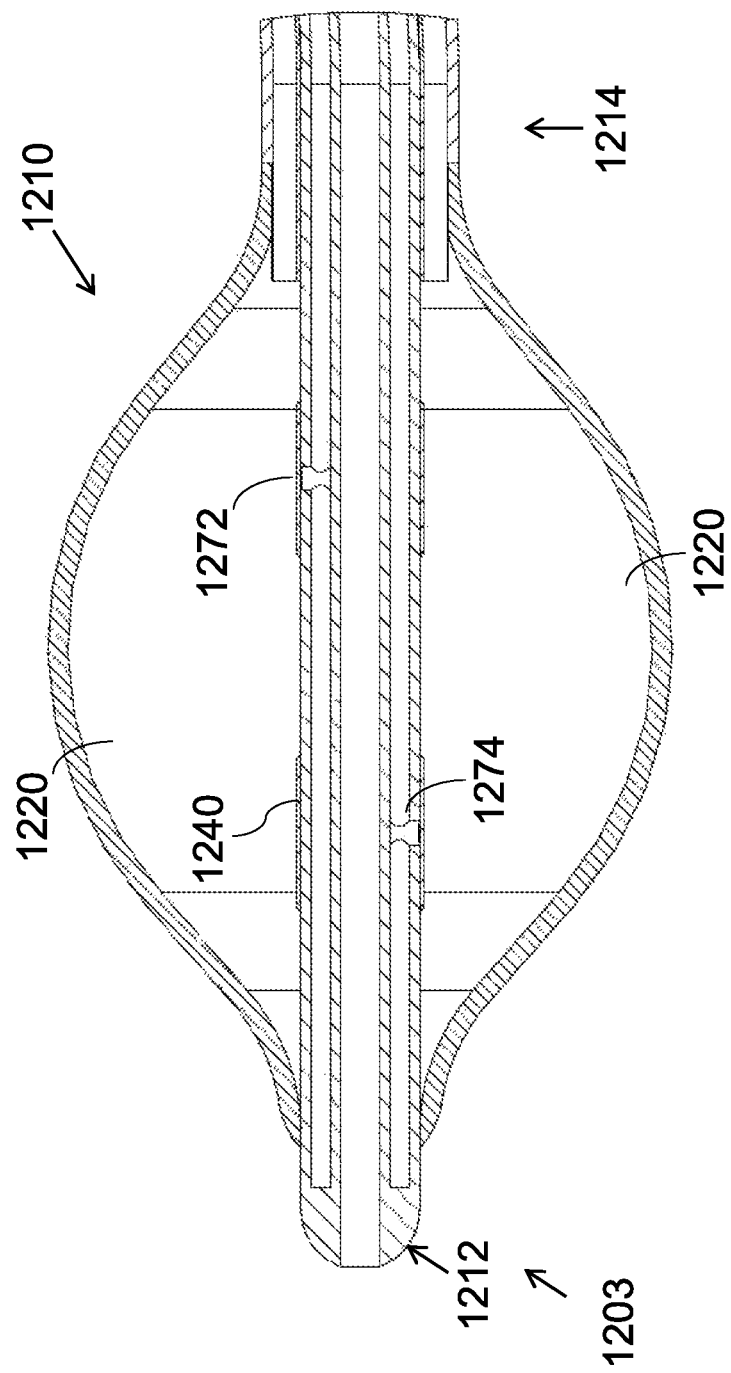
FIG. 12D is a cross-sectional view of non-limiting embodiment of a tip of the device of FIG. 12A.

With reference to FIG. 12D, the vibration source 1298 is a high energy electric pulse generator electrically connected to a first electrode 1272 and a second electrode 1274 located within the tip 1210. The first electrode 1272 and the second electrode 1274 may be located on opposite sides of the longitudinal axis of the elongated body 1204 or on the same side.

The first electrode 1272 and the second electrode 1274 are operable to receive high energy electric pulses from the vibration source 1298, i.e. the high energy electric pulse generator, and generate plasma shock waves in the conductive liquid thereby inducing mechanical vibrations at the outer surface of the inflatable balloon 1220 for destructuration of the calcified structures.

Method Description

Figure 13:
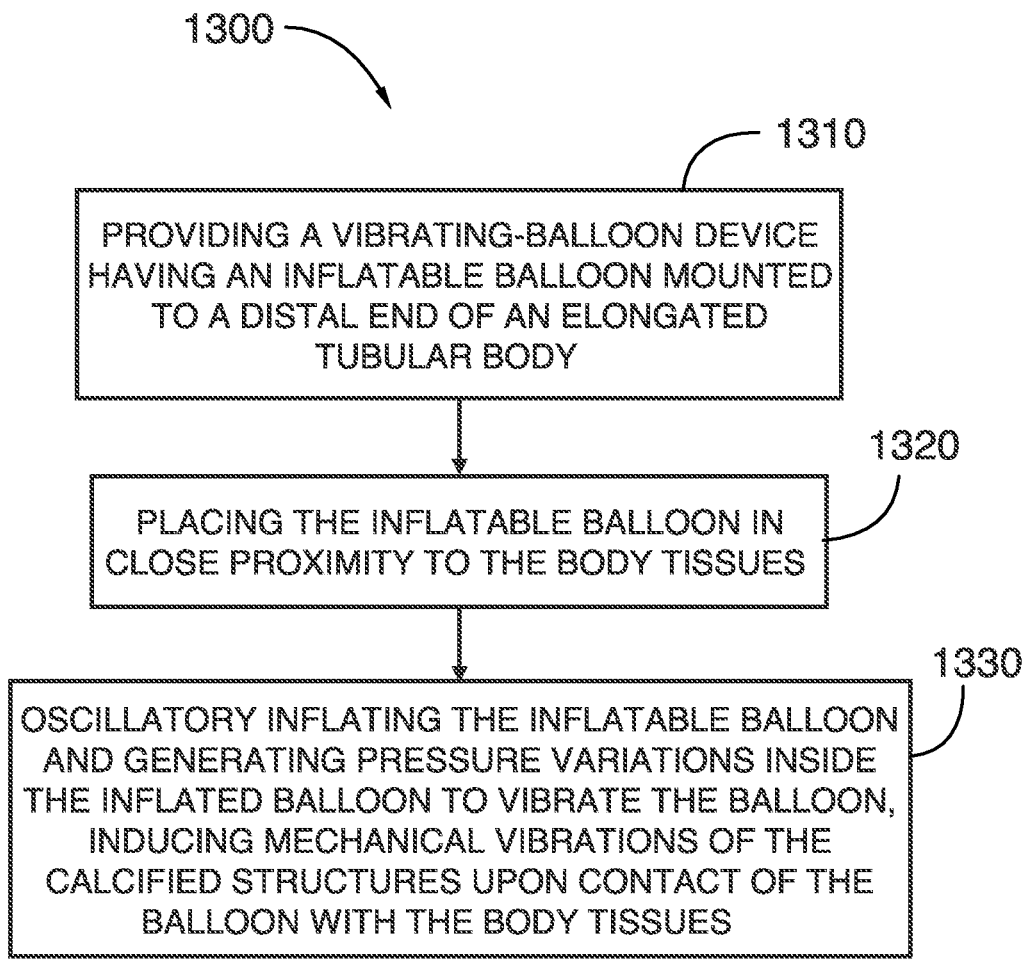
FIG. 13 is a flow chart of a method for treating calcified structures of body tissues in accordance with non-limiting embodiments of the present technology.

Referring now to FIG. 13, there is shown a flow chart of a method 1300 for treating calcified structures of body tissues, according to one embodiment. The method 1300 comprises the step 1310 of providing a vibrating-balloon device having an inflatable balloon mounted to a distal end of an elongated body, as previously described. The method 1300 comprises the step 1320 of placing the inflatable balloon in close proximity to the body tissues, as detailed above with reference to FIG. 2B and FIG. 2C. The method 1300 also comprises the step 1330 of oscillatory inflating the inflatable balloon and generating pressure variations inside the inflated balloon to vibrate the balloon, inducing mechanical vibrations of the calcified structures upon contact of the balloon with the body tissues to destructure the calcified structures.

Figure 14:
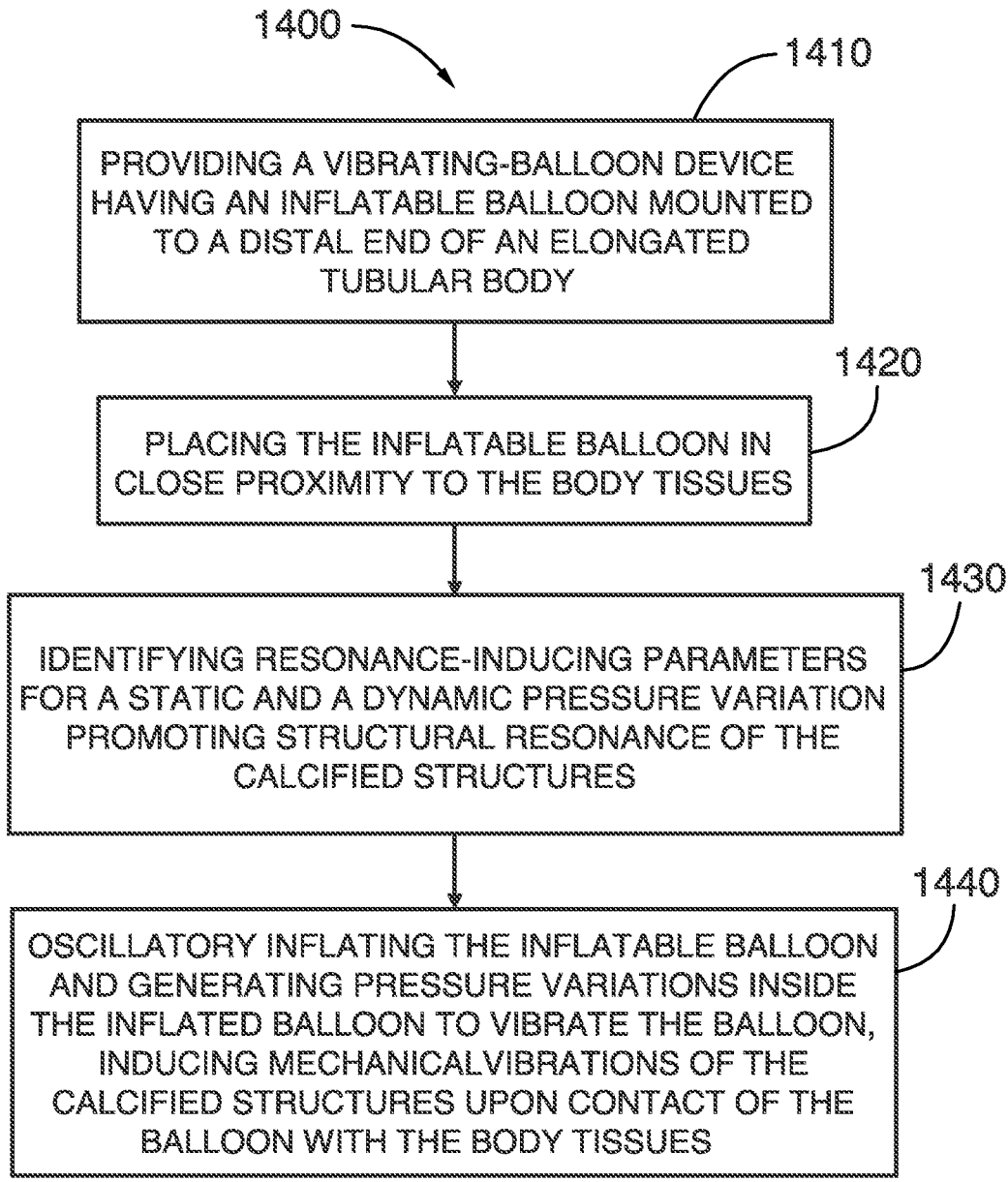
FIG. 14 is a flow chart of a method for treating calcified structures of body tissues in accordance with non-limiting embodiments of the present technology.

Referring now to FIG. 14, there is shown a flow chart of a method 1400 for treating calcified structures of body tissues, according to another embodiment. The method 1400 comprises the step 1410 of providing a vibrating-balloon device having an inflatable balloon mounted to a distal end of an elongated body, as previously described. The method 1400 comprises the step 1420 of placing the inflatable balloon in close proximity to the body tissues, as detailed above with reference to FIG. 2B and FIG. 2C. The method 1400 also comprises the step 1430 of identifying resonance-inducing parameters for the static and dynamic pressure variations that promote structural resonance of the calcified structures. The method 1400 also comprises the step 1440 of oscillatory inflating the inflatable balloon and generating pressure variations inside the inflated balloon at the aforementioned resonance-inducing identified parameters to vibrate the balloon, inducing mechanical vibrations of the calcified structures upon contact of the balloon with the body tissues to destructure the calcified structures.

Figure 15:
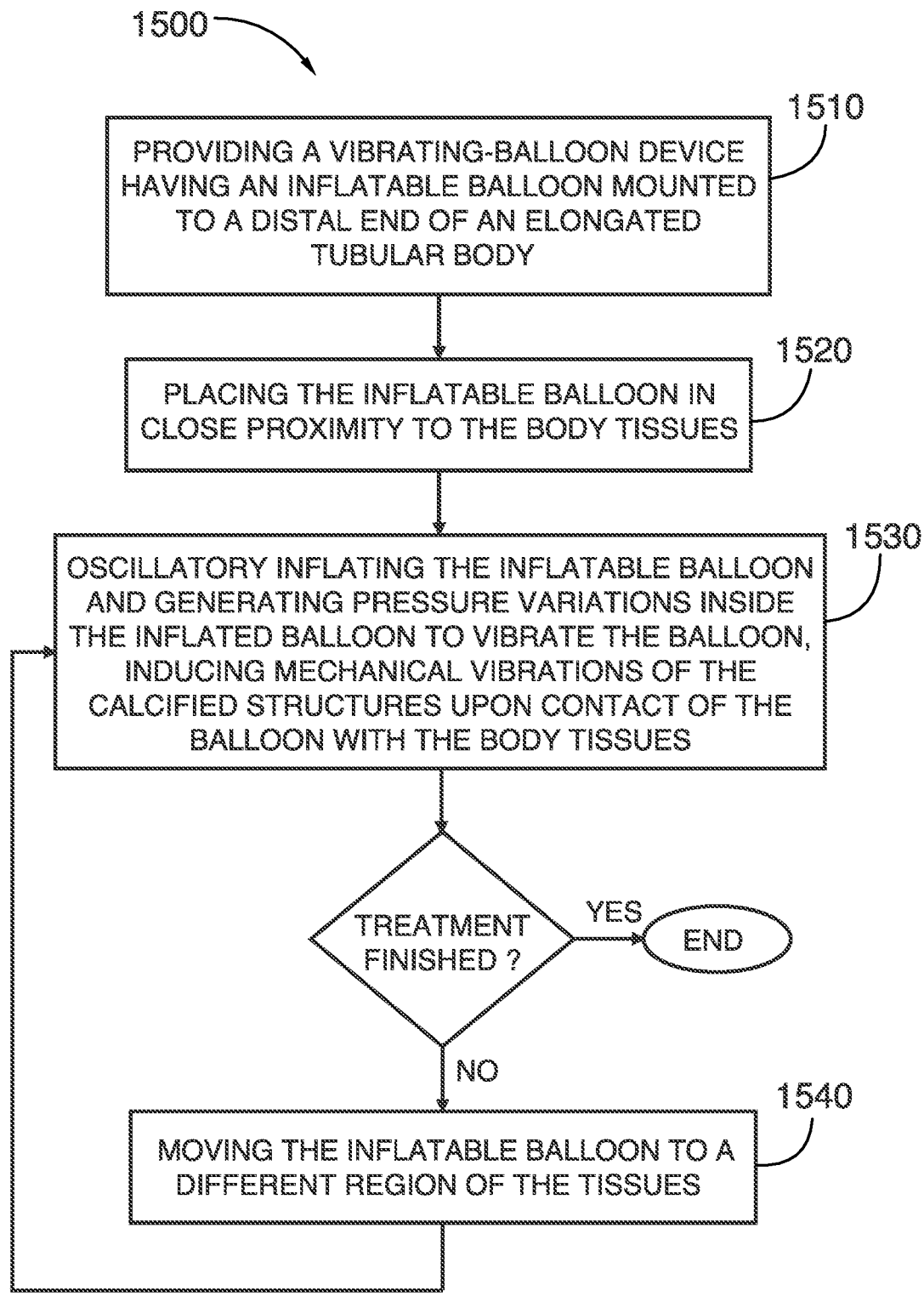
FIG. 15 is a flow chart of a method for treating calcified structures of body tissues in accordance with non-limiting embodiments of the present technology.

Referring now to FIG. 15, there is shown a flow chart of a method 1500 for treating calcified structures of body tissues, according to a further embodiment. The method 1500 comprises the step 1510 of providing a vibrating-balloon device having an inflatable balloon mounted to a distal end of an elongated body, as previously described. The method 1500 comprises the step 1520 of placing the inflatable balloon in close proximity to the body tissues, as detailed above with reference to FIG. 2B and FIG. 2C. The method 1500 also comprises the step 1530 of oscillatory inflating the inflatable balloon and generating pressure variations inside the inflated balloon to vibrate the balloon, inducing mechanical vibrations of the calcified structures upon contact of the balloon with the body tissues to destructure the calcified structures. To complete the treatment, the method 1500 further comprises the step 1540 of moving the inflatable balloon to a different region of the calcified tissues to be treated. The oscillatory inflating step 1530 and the moving step 1540 are then repeated until all the tissues containing problematic calcified structures have been treated.

Although the above description relates to specific preferred embodiments as presently contemplated by the inventors, it will be understood that the technology in its broad aspect includes mechanical and functional equivalents of the elements described herein.

What is claimed is:

1. A balloon device for treating a calcified structure of a body tissue, the balloon device comprising:
   an elongated body extending between a proximal end and a distal end and having at least one lumen extending along at least a portion thereof and defining a fluid path; and
   at least one inflatable balloon secured to the elongated body and fluidly connected to the at least one lumen, the at least one lumen being fluidly connectable to a fluid source for selectively inflating and deflating the at least one inflatable balloon, the at least one inflatable balloon for treating the calcified structure when being inflated, being positioned in close proximity to the calcified structure and vibrating, wherein mechanical vibrations of the at least one inflatable balloon causing destructuration of the calcified structure, wherein the elongated body is connectable to a light source for inducing the mechanical vibrations into the at least one inflatable balloon when inflated, and wherein the at least one inflatable balloon is adapted to receive a conductive fluid therein from the fluid source; and
   at least one transducer and at least one optical waveguide operatively connectable to the light source, and wherein the at least one transducer is operable to receive light from the light source and generate mechanical pulses in the conductive fluid to induce the mechanical vibrations of the at least one inflatable balloon.

2. The balloon device of claim 1, wherein the at least one inflatable balloon is positioned adjacent to the distal end of the elongated body.

3. The balloon device of claim 1, wherein the at least one lumen is adapted to propagate therein an oscillatory pressure fluid, the fluid source being adapted to generate pressure variations within the oscillatory pressure fluid, the pressure variations causing the mechanical vibrations of the at least one inflatable balloon.

4. The balloon device of claim 1, wherein the at least one optical waveguide comprises at least one optical fiber and the light source comprises a pulsed laser source.

5. The balloon device of claim 1, further comprising at least one temperature sensor for measuring a temperature within the at least one balloon.

6. The balloon device of claim 1, further comprising at least one monitoring sensor for measuring at least one of a filling status of the at least one inflatable balloon and a pressure within the at least one inflatable balloon.

7. The balloon device of claim 6, wherein the at least one monitoring sensor comprises one of a pressure sensor and an impedance sensor.

8. The balloon device of claim 1, wherein the elongated body further comprises a wire lumen extending within the elongated body and being sized and shaped for receiving a wire therein.

9. The balloon device of claim 1, wherein an outer surface of the at least one inflatable balloon is provided with at least one geometrical deformation.

10. A system for treating a calcified structure of a body tissue, the system comprising:
   a vibrating-balloon device comprising:
      an elongated body extending between a proximal end and a distal end and having at least one lumen extending along at least a portion of the elongated body and defining a fluid path therebetween; and
      at least one inflatable balloon connected to the at least one lumen adjacent to the distal end of the elongated body, the at least one inflatable balloon for treating the calcified structure when being inflated, being positioned in close proximity to the calcified structure and vibrating, wherein mechanical vibrations of the at least one inflatable balloon causing destructuration of the calcified structure and wherein the elongated body is connectable to a light source for inducing mechanical vibrations into the at least one inflatable balloon when inflated;
   a fluid source fluidly connectable to the at least one lumen and operable to selectively inflate and deflate the at least one inflatable balloon, wherein the at least one inflatable balloon is adapted to receive a conductive fluid therein from the fluid source; and
   at least one transducer and at least one optical waveguide operatively connectable to the light source, wherein the at least one transducer is operable to receive light from the light source and generate mechanical pulses in the conductive fluid to induce the mechanical vibrations of the at least one inflatable balloon.

11. The system of claim 10, wherein the fluid source is adapted to generate pressure variations within the conductive fluid.

12. A method for treating a calcified structure of a body tissue, the method comprising:
   providing a vibrating-balloon device comprising:
      an elongated tubular body extending between a proximal end and a distal end and having at least one lumen extending along at least a portion of the elongated tubular body and defining a fluid path therebetween;
      at least one inflatable balloon secured to the elongated tubular body and fluidly connected to the at least one lumen, the at least one inflatable balloon being provided with a transducer operable to receive light from a light source so as generate mechanical vibrations; and
      a transducer operable to receive light from a light source so as generate the mechanical vibrations;
   placing the inflatable balloon in close proximity to the body tissues;
   inflating the at least one inflatable balloon using a conductive fluid source;
   connecting an optical waveguide to the transducer; and
   propagating pulsed light along the optical waveguide, thereby generating the mechanical vibrations within the at least one inflated balloon, thereby inducing mechanical vibrations of the calcified structure upon contact of the balloon with the body tissues to destruct the calcified structure.

13. The method of claim 12, further comprising, before the oscillatory inflating the at least one inflatable balloon:
   identifying resonance-inducing parameters for a static and a dynamic pressure variation that promote structural resonance of the calcified structure.

14. The method of claim 12, further comprising:
   moving the at least one inflatable balloon to a different region of the tissues; and
   repeating the oscillatory and the moving until each calcified structure has been treated.

* * * * *